United States Patent
Berge et al.

(10) Patent No.: US 10,821,060 B2
(45) Date of Patent: Nov. 3, 2020

(54) PROCESS FOR SHORT-TERM IMPROVEMENT OF THE MOISTURIZATION STATE OF HUMAN SKIN EPIDERMIS; NOVEL MOISTURIZING COMPOSITIONS

(71) Applicant: SOCIETE D'EXPLOITATION DE PRODUITS POUR LES INDUSTRIES CHIMIQUES SEPPIC, Paris (FR)

(72) Inventors: Armelle Berge, Castres (FR); Laetitia Cattuzzato, Castres (FR); Sandy Dumont, Caucalieres (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 47 days.

(21) Appl. No.: 16/098,446

(22) PCT Filed: Apr. 28, 2017

(86) PCT No.: PCT/FR2017/051022
§ 371 (c)(1),
(2) Date: Nov. 2, 2018

(87) PCT Pub. No.: WO2017/191394
PCT Pub. Date: Nov. 9, 2017

(65) Prior Publication Data
US 2019/0151211 A1    May 23, 2019

(30) Foreign Application Priority Data

May 4, 2016 (FR) ........................ 16 54060

(51) Int. Cl.
*A61K 8/34* (2006.01)
*A61K 8/60* (2006.01)
*A61Q 19/00* (2006.01)

(52) U.S. Cl.
CPC .............. *A61K 8/345* (2013.01); *A61K 8/604* (2013.01); *A61Q 19/00* (2013.01); *A61Q 19/007* (2013.01)

(58) Field of Classification Search
CPC ...... A61K 8/345; A61K 8/604; A61Q 19/007; A61Q 19/00
See application file for complete search history.

(56) References Cited

FOREIGN PATENT DOCUMENTS

| WO | WO 03/094864 | 11/2003 |
|---|---|---|
| WO | WO 2007/113440 | 10/2007 |
| WO | WO 2014/154958 | 10/2014 |

OTHER PUBLICATIONS

International Search Report, PCT/FR2017/051022, dated Jul. 19, 2017.
French Search Report, FR 1654060, dated Dec. 6, 2016.

*Primary Examiner* — Lawrence E Crane
(74) *Attorney, Agent, or Firm* — Nixon & Vanderhye

(57) ABSTRACT

A process and composition for improvement of the moisturization state of the stratum corneum of human skin epidermis comprising applying to the skin an effective amount of a composition (C) for topical use comprising at least one cosmetically acceptable excipient and a composition C1 consisting of 20-50% by weight of composition C2, which in turn includes from 3-25% by weight of a polyol, from 25-45% by weight anhydrides of the polyol, and from 30-72% by weight of polyol glycosides of the polyol, with the remainder of composition C2 to 100% by weight being made up of water; and from 50-80% by weight of glycerol and/or glycerol oligomers, with the ratio of polyol glycosides to glycerol and/or glycerol oligomers greater than or equal to 1/10 and less than or equal to 1/2.

19 Claims, No Drawings

PROCESS FOR SHORT-TERM IMPROVEMENT OF THE MOISTURIZATION STATE OF HUMAN SKIN EPIDERMIS; NOVEL MOISTURIZING COMPOSITIONS

A subject of the present invention is the use of compositions for topical use based on polyol glycosides and on glycerol and/or glycerol oligomers, for short-term moisturization of the skin. A subject of the present invention is also novel compositions for topical use based on polyol glycosides and on glycerol oligomers.

The invention mainly applies in the cosmetics and dermopharmacy fields, but also in the field of the textile industry, for example for the treatment of woven or knitted synthetic or natural textile fibers, or else in the field of the papermaking industry, for example for the manufacture of paper for sanitary or domestic use.

The skin is an atypical organ of the human body, extremely fine from the viewpoint of its extent, but also the heaviest organ of an individual. One of the characteristics of the skin lies in the fact that it is an interface organ, a limiting organ, between the inside environment (human body) and the outside environment. As a result, and with the flora which covers it and lives on it, the skin is the first barrier for protection of the human organism.

Because of its position of interface with the outside environment, the skin is subjected to numerous daily stresses, such as for example contact with clothing, temperature changes, changes in degrees of hygrometry, pressure changes, or even to attacks, such as for example contact with certain chemical products which have or may have a very acid, or very basic, or irritant nature, or with chemical products considered to be polluting agents.

The skin is composed of layers of different tissues:
the epidermis, composed of keratinocytes, is its outermost part, then comes
the dermis, which is a connective tissue composed mainly of fibroblasts and of the extracellular matrix, and
the hypodermis, consisting of adipocytes, which is the part that is the deepest and the furthest away from the outside environment.

The skin ensures various functions in the interests of the entire system that it shelters, among which may be retained:
a mechanical barrier function in order to guarantee the integrity of the inner environment of the organism,
an emunctory function aimed at secreting sweat based on water, salts and acid waste,
a body temperature regulation function, and contains many other regulation mechanisms, for instance its mechanism of adaptation and protection against ultraviolet radiation (adaptive pigment coloration through melamin production), for instance an immune surveillance system to the presence of macrophages and of dendritic cells.

Human skin also constitutes the first image offered to the viewpoint of others. Consequently, improving one's appearance is a subject of constant preoccupation for human beings. The skin is the reflection of a state of wellbeing, often associated with youthfulness and, conversely with a state of fatigue and/or of aging. As a result, the preservation, the improvement, of the state of the outermost layer of the skin, namely the epidermis, constitutes a center of major interest for research carried out by the cosmetic industries.

At the periphery of the epidermis is an upper horny layer, called the stratum corneum, which is the first layer of the epidermis to undergo stresses of external origin, such as variations in outside climatic conditions (temperature, pressure, hygrometry) or mechanical stresses. Consequently, improving the appearance or maintaining the good appearance of human skin consists in particular in maintaining the moisturization state of the stratum corneum at an optimal and satisfactory level. This in addition makes it possible to avoid the esthetic and physiological drawbacks associated with a state of dryness of the skin.

The stratum corneum has a tendency to dehydrate and to dry out when it is exposed to a low humidity or when it is brought into prolonged and frequent contact with a detergent solution.

Many solutions have already been provided to solve the problems of dryness of the skin caused by dehydration of the stratum corneum, in particular by the development of moisturizing compositions.

However, in order to prevent the skin from deteriorating too rapidly, it is necessary to provide a short-term moisturization of the skin, which acts in a short period of time, in particular in the case of exposure of the hands, lips and face to climatic conditions (intense cold, wind) which induce rapid drying out of the skin.

In order to evaluate and account for the "good health" of the skin, and of its "good functional state", and more particularly of "its moisturization", two measurements are commonly used, because of their reliability and their robustness:
the measurement of the degree of moisturization in the stratum corneum, that is to say the water content within it, and
the measurement of the insensible water loss (or IWL), that is to say the flow of water evaporating from the skin via the stratum corneum, because of the passive diffusion of water from the deepest layers of the skin to the external environment and because of perspiration, which can be detected at any time at its surface.

The degree of moisturization of the skin is measured by biometrological techniques, in particular based on measurements of the capacitance of the skin or the impedance of the skin. Various commercial items of equipment are available for carrying out such measurements. An increase in impedance or in capacitance indicates an increase in the degree of moisturization of the skin and, consequently, in the water content in the stratum corneum.

The insensible water loss (or IWL) is measured by biometrological techniques consisting of the application, to the surface of the skin and under standardized conditions, of an instrument consisting of an open cylinder in which a probe measures, dynamically, the water evaporation flow. In addition to this conventional open cylinder technique, similar instruments, based on a closed cylinder (closed chamber) technique, have more recently been developed and are also available. A decrease in "insensible water loss" measured at the surface of stratum corneum indicates a reduction in the evaporation of the water contained.

From the viewpoint of these previous definitions, an improvement in the moisturization of the skin, and more particularly of the stratum corneum, can be conceived by bringing the skin into contact with compounds which have a "moisturizing effect".

For the purposes of the present application, the term "moisturizing effect" is intended to mean an increase in the degree of moisturization of the stratum corneum resulting from the topical application of a chemical substance or of a chemical composition on the surface of the skin to be treated.

For the purposes of the present application, the term "short-term moisturizing effect" is intended to mean an increase in the degree of moisturization of the stratum corneum, measured and observed within a period of between three and eight hours, and resulting from the single topical application of a chemical substance or of a chemical composition on the surface of the skin to be treated.

For the purposes of the present application, the term "long-term moisturizing effect" is intended to mean:

an increase in the degree of moisturization of the stratum corneum, measured within a period greater than or equal to twenty-four hours, resulting from the single application of a chemical substance or of a chemical composition on the surface of the skin to be treated, or a measured increase in the degree of moisturization of the stratum corneum, resulting from repeated applications of the same substance or composition, over several days or several weeks. This increase can be considered to be an effect obtained through the combination of the direct moisturizing action due to the substance or to the composition applied, and of the indirect action obtained by means of the biochemical and structural modifications having taken place in the skin by virtue of the application of the substance or of the composition (biological effect of an active ingredient).

For the purposes of the present application, the term "occlusive effect" is intended to mean a decrease in insensible water loss, as previously defined, measured at the surface of the skin at the level of the stratum corneum.

For the purposes of the present application, the term "immediate occlusive effect" is intended to mean a decrease in insensible water loss, as previously defined, taking effect in a short period of time, for example a period between 30 minutes and one hour after the topical application of a chemical substance or of a chemical composition on the surface of the skin to be treated.

A challenge of moisturization of the skin, and therefore of the research studies which are associated therewith, is to develop substances or compositions which are characterized by an improved moisturizing effect without however having to induce a considerable occlusive effect, said occlusive effect possibly causing disruptions to the natural operation of "non-pathological" skin, namely skin which does not exhibit an insensible water loss greater than 10 $g/m^2/h$, and therefore proving to be contrary to the desired objective.

As skin-moisturizing agent, and more particularly agent for moisturizing very dry and destructed skin, there are:

occlusive agents which are characterized by their ability to form an impermeable film at the surface of the skin and to thus greatly decrease water evaporation at the surface of the epidermis. Such agents are, for example, mineral oils such as petroleum jelly or paraffin oils, glycerol, shea butter (Butyrospermum parkii butter), beeswax (Cera alba), certain vegetable oils such as wheatgerm oil, coconut oil, cacao butter, lanolin and silicone derivatives;

emollients which are characterized by their ability to fill the intercellular spaces which are between the corneocytes (cells of the horny layer of the epidermis); they also limit water evaporation from the epidermis, but to a lesser extent than occlusive agents. Such agents are, for example, ceramides, linoleic acid and certain vegetable oils such as sweet almond oil or jojoba oil;

film-forming agents, which are characterized by their ability to combine with water so as to form semipermeable hydrogels; they thus contribute to modulating water evaporation from the stratum corneum. Such agents are, for example, collagen, elastin, DNA, pectin, gelatin, chitosan, or glycosaminoglycans such as hyaluronic acid;

humectants, which are hydrophilic substances characterized by their strong hygroscopic power, namely their ability to retain water. They thus contribute to enabling the stratum corneum to retain both the water that it contains, and that provided by the cosmetic formula. Such agents are, for example, urea, glycerol, lactic acid, amino acids, sodium lactate, propylene glycol, polyethylene glycols, alpha-hydroxy acids or sorbitol. Glycerol, urea and lactic acid are the humectants most widely used in moisturizing cosmetic compositions, and most particularly glycerol because of its very competitive cost.

However, some humectants, such as glycerol, also have an immediate occlusive effect, which is not desired for normal skin, the barrier function of which is not deficient. Furthermore, some of them, such as also glycerol, cause some irritations of the skin and mucous membranes in particularly sensitive individuals.

The research for new moisturizing substances, which are better tolerated than glycerol, has in particular resulted in the use of certain glyercol derivatives, in particular glycerol acetals, resulting from its condensation with a reducing sugar. Mention may in particular be made of:

the acetals resulting from the condensation of glycerol with glucose, which are disclosed in the European patent application published under number EP 0 770 378; they effectively exhibit a better skin tolerance than glycerol, but have a generally lower moisturizing capacity;

the mannosyl erythritol described in the Japanese patent application published under number JP 63063390 A2, which is obtained according to an enzymatic preparation process, and known for its skin moisturization-retaining activity.

Among the acetals of glucose and other polyols, mention may be made of the glycosides obtained by acetalization of erythritol, of xylitol or of sorbitol, as described in the French patent application published under number FR 2 839 447 A1. These compounds have demonstrated better moisturizing properties than the abovementioned glycerol acetalization products.

Synergistic compositions of pullulan or a derivative thereof with hyaluronic acid and/or alginic acid, and/or a salt or derivative thereof, are disclosed in the International application published under number WO 2014/027163, as improving, in the short term, the moisturization state of the superficial layers of human skin.

The European patent application published under number EP 2011476 A2 discloses moisturizing compositions containing, in variable and defined proportions, urea, a betain, glycerol, and at least one improving agent chosen from *Imperata cylindrica* extracts, yeast extracts and xylityl glycosides, and also the use thereof for long-term moisturization of the skin.

In the context of their research regarding the improvement of skin moisturization, the inventors have endeavored to develop a new technical solution based on the use of particular compositions based on polyol glycosides and on glycerol or glycerol oligomer, for increasing the short-term degree of moisturization of the superficial layers of the skin, and more particularly of the stratum corneum of the epidermis of human skin, without inducing an increase in insensible water loss of said stratum corneum.

Thus, according to a first aspect, a subject of the invention is a process for short-term improvement of the moisturization state of the stratum corneum of human skin epidermis, characterized in that it comprises at least one step a) of applying, to the surface of the skin to be treated, an effective amount of a composition for topical use (C) comprising at least one cosmetically acceptable excipient (E) and a composition ($C_1$) consisting of, for 100% of the weight thereof:

(a)—from 20% by weight to 50% by weight of at least one composition ($C_2$), said composition ($C_2$) consisting of, for 100% of the weight thereof:

(1)—from 3% to 25% by weight of a polyol of formula (I):

$$HO-CH_2-(CHOH)_m-CH_2-OH \quad (I);$$

in which formula (I) m represents an integer equal to 2, 3 or 4;

(2)—from 25% to 45% by weight of one or more anhydrides of said polyol of formula (I);

(3)—from 30% to 72% by weight of a composition ($C_A$) represented by formula (II):

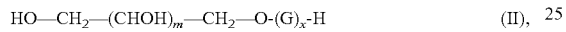

$$HO-CH_2-(CHOH)_m-CH_2-O-(G)_x-H \quad (II),$$

in which formula (II) G represents the residue of a reducing sugar, m is as previously defined in formula (I) and x, which indicates the average degree of polymerization of said residue G, represents a decimal number greater than 1 and less than or equal to 5, and (4)—the remainder to 100% by weight being made up of water; and (b)—from 50% by weight to 80% by weight of at least one compound of formula (III):

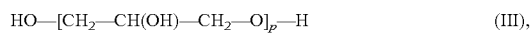

$$HO-[CH_2-CH(OH)-CH_2-O]_p-H \quad (III),$$

in which formula (III) p represents an integer greater than or equal to 1 and less than or equal to 6, it being understood that, in said composition ($C_1$), the composition ($C_A$)/compound of formula (III) weight ratio is greater than or equal to 1/10 and less than or equal to 1/2.

The term "anhydride of the polyol of formula (I)" denotes in particular:

when m is equal to 2, the compound of formula ($B_{11}$):

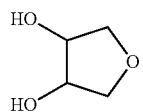

(B11)

when m is equal to 3, the compound of formula ($B_{12}$):

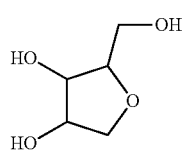

(B12)

and, when m is equal to 4, the compounds of formulae ($B_{13}$):

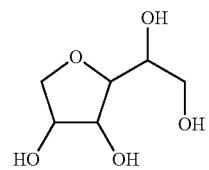

(B13)

and

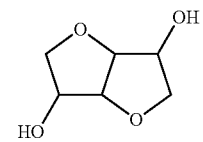

(B14)

($B_{14}$):

For the purposes of the present application, the expression "short-term improvement in the moisturization state of the stratum corneum of human skin epidermis" is intended to mean:

an increase in the degree of moisturization of the stratum corneum of human skin epidermis, measured and observed within a period of between three hours and eight hours after the application of said composition for topical use (C) to the surface of said stratum corneum of human skin epidermis, of greater than or equal to 40% relative to the degree of moisturization measured and observed before the application of said composition for topical use (C), to the surface of said stratum corneum of the human skin epidermis to be treated, and a decrease in the insensible water loss of the human skin epidermis, measured and observed within a period of between 30 minutes and 60 minutes after the application, to the surface to be treated of said stratum corneum of human skin epidermis, of said composition for topical use (C) of less than or equal to 10% relative to the insensible water loss measured and observed before application of said composition for topical use (C) to the surface of the human skin epidermis to be treated.

The term "effective amount" denotes, in the definition of the process as defined above, an amount such that the moisturization state of the stratum corneum of the human skin epidermis obtained after application to the epidermis of the skin to be treated shows:

an increase in the degree of moisturization of the stratum corneum of the human skin epidermis treated of greater than 40% relative to the degree of moisturization measured before the application of the topical composition (C) to the surface of the skin epidermis to be treated, after a period of between three hours and eight hours after the application of said composition (C) to said surface of the epidermis to be treated, and a decrease in the insensible water loss of the human skin epidermis treated of less than or equal to 10% relative to the value of the insensible water loss measured before the application of the topical composition (C) to the surface of the skin epidermis to be treated, after a period of between 30 minutes and 60 minutes after the application of said composition (C) to said surface of the epidermis to be treated.

The expression "for topical use" used in the definition of the process as defined above means, for the purposes of the present invention, that said composition (C) is used by application to the skin, the scalp or the mucous membranes, regardless of whether it is a direct application in the case of a cosmetic, dermocosmetic, dermopharmaceutical or pharmaceutical composition or an indirect application, for example in the case of a body hygiene product or a skin care or protection product, which is in the form of a textile item, for example a wipe, or a paper item, for instance a paper for sanitary use.

The term "reducing sugar" denotes, in formula (II) as previously defined, the saccharide derivatives which do not exhibit, in their structures, any glycosidic bond established between an anomeric carbon and the oxygen of an acetal group, as defined in the reference work: "Biochemistry", Daniel Voet/Judith G. Voet, p. 250, John Wyley & Sons, 1990. The oligomeric structure $(G)_x$ can be in any forms of isomerism, whether optical isomerism, geometric isomerism or positional isomerism; it can also represent a mixture of isomers.

The term "compound of formula (III)" as previously defined denotes glycerol when p is equal to 1, diglycerol when p is equal to 2, triglycerol when p is equal to 3, tetraglycerol when p is equal to 4, pentaglycerol when p is equal to 5 and hexaglycerol when p is equal to 6.

According to one particular aspect of the present invention, said composition $(C_1)$ consists of, for 100% by weight:
- (a)—from 20% by weight to 40% by weight, and more particularly from 20% to 35% by weight of said composition $(C_2)$,
- (b)—from 60% by weight to 80% by weight and more particularly from 65% by weight to 80% by weight of at least one compound of formula (III).

According to another particular aspect of the present invention, the composition $(C_2)$ consists of, for 100% of the weight thereof:
- (1)—from 5% to 20% by weight of a polyol of formula (I) as previously defined;
- (2)—from 25% to 35% by weight of one or more anhydrides of said polyol of formula (I);
- (3)—from 45% to 70% by weight of said composition $(C_A)$ as previously defined, and
- (4)—the remainder to 100% by weight being made up of water.

According to another particular aspect of the present invention, in said composition $(C_1)$, the composition $(C_A)$/compound of formula (III) weight ratio is greater than or equal to 1/7 and less than or equal to 1/4.

According to another particular aspect, the composition $(C_1)$ as previously defined is characterized in that, in formula (II), said residue G of a reducing sugar is chosen from the residues of glucose, dextrose, sucrose, fructose, idose, gulose, galactose, maltose, isomaltose, maltotriose, lactose, cellobiose, mannose, ribose, xylose, arabinose, lyxose, allose, altrose, dextran or tallose. According to a more particular aspect, said residue G of a reducing sugar is chosen from the residues of glucose, xylose and arabinose, and most particularly G represents the residue of glucose.

The term "formula (II) HO—$CH_2$—$(CHOH)_n$—$CH_2$—O-$(G)_x$-H" means that said composition $(C_A)$ consists essentially of a mixture of compounds represented by formulae $(II_1)$, $(II_2)$, $(II_3)$, $(II_4)$ and $(II_5)$:

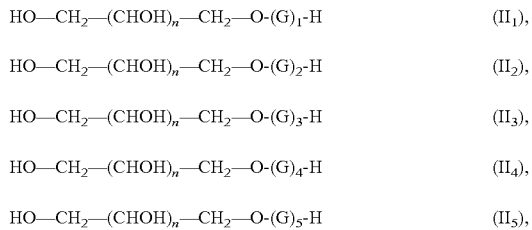

in the respective molar proportions $a_1$, $a_2$, $a_3$, $a_4$ and $a_5$, such that the sum $a_1+a_2+a_3+a_4+a_5$ is equal to 1 and that the sum $a_1+2a_2+3a_3+4a_4+5a_5$ is equal to x.

The term "essentially" indicates, in the preceding definition, that the presence of one or more compounds of formula $(II_w)$ with w greater than 5 is not excluded in the composition $(C_A)$, but that, if it is present, it is present in minimal proportions which do not bring about any substantial modification of the properties of said composition $(C_A)$.

In formula (II) as defined above, the group HO—$CH_2$—$(CHOH)_n$—$CH_2$—O— is bonded to $(G)_x$ by the anomeric carbon of the saccharide residue, so as to form an acetal function.

According to a more particular aspect, a subject of the invention is a process as previously defined, wherein, in formula (II), x represents a decimal number greater than or equal to 1.05 and less than or equal to 3, and most particularly greater than or equal to 1.15 and less than or equal to 2.5.

According to another more particular aspect, a subject of the invention is a process as previously defined, wherein, in the definition of the composition $(C_A)$ represented by formula (II) and as previously defined, said residue G of a reducing sugar is chosen from the residues of glucose, xylose and arabinose and x represents a decimal number greater than or equal to 1.05 and less than or equal to 3, more particularly greater than or equal to 1.15 and less than or equal to 2.5.

According to another particular aspect, a subject of the invention is a process as previously defined, wherein, in formulae (I) and (II), m is equal to 2.

According to another particular aspect, a subject of the invention is a process as previously defined, wherein, in formulae (I) and (II), m is equal to 3.

According to another particular aspect, a subject of the invention is a process as previously defined, wherein, in formulae (I) and (II), m is equal to 4.

According to one particular aspect, a subject of the invention is a process as previously defined, wherein, in formula (III), p is equal to 1 or to 2, and most particularly equal to 1.

According to another particular aspect, a subject of the invention is a process as previously defined, wherein, in formulae (I) and (II), m is equal 2, in formula (II), said residue G of a reducing sugar represents the residue of glucose, and x represents a decimal number between 1.05 and 2.5, and in formula (III), p is equal to 1 or to 2, and more particularly equal to 1.

According to another particular aspect, a subject of the invention is a process as previously defined, wherein, in formulae (I) and (II), m is equal to 3, in formula (II), said residue G of a reducing sugar represents the residue of glucose, and x represents a decimal number between 1.05 and 2.5, and in formula (III), p is equal to 1 or to 2, and more particularly equal to 1.

According to another particular aspect, a subject of the invention is a process as previously defined, wherein, in formulae (I) and (II), m is equal to 4, in formula (II) said residue G of a reducing sugar represents the residue of glucose, and x represents a decimal number between 1.05 and 2.5, and in formula (III), p is equal to 1 or to 2, and more particularly equal to 1.

A subject of the invention is also a composition $(C_1)$ consisting of, for 100% of the weight thereof:
- (a)—from 20% by weight to 50% by weight of at least one composition $(C_2)$, said composition $(C_2)$ consisting of, for 100% of the weight thereof:

(1)—from 3% to 25% by weight of a polyol of formula (I):

HO—CH$_2$—(CHOH)$_m$—CH$_2$—OH　　(I);

in which formula (I) m represents an integer equal to 2, 3 or 4;

(2)—from 25% to 45% by weight of one or more anhydrides of said polyol of formula (I);

(3)—from 30% to 72% by weight of a composition (C$_A$) represented by formula (II):

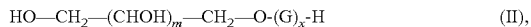
HO—CH$_2$—(CHOH)$_m$—CH$_2$—O-(G)$_x$-H　　(II), in which formula (II) G represents the residue of a reducing sugar, m is as previously defined in formula (I) and x, which indicates the average degree of polymerization of said residue G, represents a decimal number greater than 1 and less than or equal to 5, and (4)—the remainder to 100% by weight being made up of water; and (b)—from 50% by weight to 80% by weight of at least one compound of formula (III):

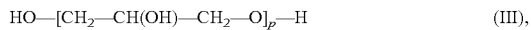
HO—[CH$_2$—CH(OH)—CH$_2$—O]$_p$—H　　(III), in which formula (III) p represents an integer greater than or equal to 1 and less than or equal to 6, it being understood that, in said composition (C$_1$), the composition (C$_A$)/compound of formula (III) weight ratio is greater than or equal to 1/10 and less than or equal to 1/2.

The term "anhydride of the polyol of formula (I)" denotes in particular:

when m is equal to 2, the compound of formula (B$_{11}$):

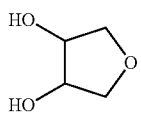
(B11)

when m is equal to 3, the compound of formula (B$_{12}$):

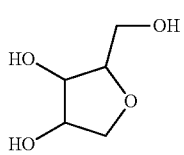
(B12)

and, when m is equal to 4, the compounds of formulae (B$_{13}$):

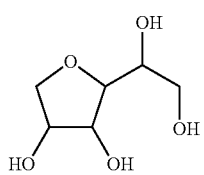
(B13)

and

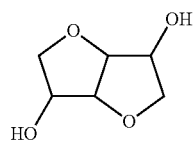
(B14)

The term "reducing sugar" denotes, in formula (II) as previously defined, the saccharide derivatives which do not exhibit, in their structures, any glycosidic bond established between an anomeric carbon and the oxygen of an acetal group, as defined in the reference work: "Biochemistry", Daniel Voet/Judith G. Voet, p. 250, John Wyley & Sons, 1990. The oligomeric structure (G)$_x$ can be in any forms of isomerism, whether optical isomerism, geometric isomerism or positional isomerism; it can also represent a mixture of isomers.

According to another particular aspect, a subject of the invention is a composition (C$_1$) as previously defined, characterized in that, in formula (II), said residue G of a reducing sugar is chosen from the residues of glucose, dextrose, sucrose, fructose, idose, gulose, galactose, maltose, isomaltose, maltotriose, lactose, cellobiose, mannose, ribose, xylose, arabinose, lyxose, allose, altrose, dextran or tallose. According to a more particular aspect, said residue G of a reducing sugar is chosen from the residues of glucose, xylose and arabinose, and most particularly G represents the residue of glucose.

The term "compound of formula (III) as previously defined" denotes glycerol when p is equal to 1, diglycerol when p is equal to 2, triglycerol when p is equal to 3, tetraglycerol when p is equal to 4, pentaglycerol when p is equal to 5 and hexaglycerol when p is equal to 6.

According to an even more particular aspect, a subject of the invention is a composition (C$_1$) as previously defined, wherein, in formula (II), p represents an integer equal to 1 or equal to 2.

According to one particular aspect of the present invention, said composition (C$_1$) consists of, for 100% by weight:

(a)—from 20% by weight to 40% by weight, and more particularly from 20% to 35% by weight of said composition (C$_2$), (b)—from 60% by weight to 80% by weight and more particularly from 65% by weight to 80% by weight of at least one compound of formula (III).

According to another particular aspect of the present invention, the composition (C$_2$) consists of, for 100% of the weight thereof:

(1)—from 5% to 20% by weight of a polyol of formula (I) as previously defined;

(2)—from 25% to 35% by weight of one or more anhydrides of said polyol of formula (I);

(3)—from 45% to 70% by weight of said composition (C$_A$) as previously defined, and (4)—the remainder to 100% by weight being made up of water.

According to another particular aspect of the present invention, in said composition (C$_1$), the composition (C$_A$)/compound of formula (III) weight ratio is greater than or equal to 1/7 and less than or equal to 1/4.

The term "formula (II) HO—CH$_2$—(CHOH)$_n$—CH$_2$—O-(G)$_x$-H" means that said composition (C$_A$) consists essentially of a mixture of compounds represented by formulae $(II_D)$, $(II_2)$, $(II_3)$, $(II_4)$ and $(II_5)$:

$$HO-CH_2-(CHOH)_n-CH_2-O-(G)_1-H \quad (II_1),$$

$$HO-CH_2-(CHOH)_n-CH_2-O-(G)_2-H \quad (II_2),$$

$$HO-CH_2-(CHOH)_n-CH_2-O-(G)_3-H \quad (II_3),$$

$$HO-CH_2-(CHOH)_n-CH_2-O-(G)_4-H \quad (II_4),$$

$$HO-CH_2-(CHOH)_n-CH_2-O-(G)_5-H \quad (II_5),$$

in the respective molar proportions $a_1$, $a_2$, $a_3$, $a_4$ and $a_5$, such that the sum $a_1+a_2+a_3+a_4+a_5$ is equal to 1 and that the sum $a_1+2a_2+3a_3+4a_4+5a_5$ is equal to x.

The term "essentially" indicates, in the preceding definition, that the presence of one or more compounds of formula $(II_w)$ with w greater than 5 is not excluded in the composition $(C_A)$, but that, if it is present, it is present in minimal proportions which do not bring about any substantial modification of the properties of said composition $(C_A)$.

In formula (II) as defined above, the group:

$$HO-CH_2-(CHOH)_n-CH_2-O-$$

is bonded to $(G)_x$ by the anomeric carbon of the saccharide residue, so as to form an acetal function.

According to a more particular aspect, a subject of the invention is the composition $(C_2)$ as previously defined, wherein, in formula (II), x represents a decimal number greater than or equal to 1.05 and less than or equal to 3, and most particularly greater than or equal to 1.15 and less than or equal to 2.5.

According to another more particular aspect, a subject of the invention is the composition $(C_2)$ as previously defined, characterized in that, in formula (II), said residue G of a reducing sugar is chosen from the residue of glucose, xylose and arabinose, and x represents a decimal number greater than or equal to 1.05 and less than or equal to 3.0.

According to another particular aspect, a subject of the invention is the composition $(C_2)$ as previously defined, wherein, in formulae (I) and (II), m is equal to 2.

According to another particular aspect, a subject of the invention is the composition $(C_2)$ as previously defined, wherein, in formulae (I) and (II), m is equal to 3.

According to another particular aspect, a subject of the invention is the composition $(C_2)$ as previously defined, wherein, in formulae (I) and (II), m is equal to 4.

According to one particular aspect, a subject of the invention is the composition $(C_2)$ as previously defined, wherein, in formula (III), p is equal to 1 or to 2, and most particularly equal to 1.

According to another particular aspect, a subject of the invention is the composition $(C_1)$ as previously defined, wherein, in formulae (I) and (II), m is equal to 2, in formula (II), said residue G represents the residue of glucose, and x represents a decimal number between 1.05 and 2.5 and, in formula (III), p is equal to 1 or equal to 2 and more particularly equal to 1.

According to another particular aspect, a subject of the invention is the composition $(C_1)$ as previously defined, wherein, in formulae (I) and (II), m is equal to 3, in formula (II), said residue G represents the residue of glucose, and x represents a decimal number between 1.05 and 2.5 and, in formula (III), p is equal to 1 or equal to 2 and more particularly equal to 1.

According to another particular aspect, a subject of the invention is the composition $(C_1)$ as previously defined, wherein, in formulae (I) and (II), m is equal to 4, in formula (II), said residue G represents the residue of glucose, and x represents a decimal number between 1.05 and 2.5 and, in formula (III), p is equal to 1 or equal to 2 and more particularly equal to 1.

The composition $(C_1)$ which is a subject of the invention can be obtained by various routes:

A first synthesis route consists in introducing each of the constituents, composition $(C_A)$, compound of formula (I), anhydride of said compound and compound of formula (III), into a reactor according to a desired weight ratio, and stirring this mixture at an effective mechanical stirring, under temperature conditions which make it possible to ensure its homogeneity, preferentially between 20° C. and 90° C.

A second synthesis route for the composition $(C_1)$ which is a subject of the invention consists in synthesizing the composition $(C_A)$ during a first step $(a_2)$, by dispersing a reducing sugar on a polyol of formula (I), such as erythritol, xylitol or sorbitol, previously brought to a temperature at least 5° C. higher $(T_1)$ than its melting point in a reactor, according to the desired stoichiometric ratio, and in subjecting this mixture to an acetalization reaction under predetermined temperature and partial vacuum conditions in the presence of an acid catalytic system. The components of this acid catalytic system will generally be chosen from sulfuric acid, hydrochloric acid, phosphoric acid, nitric acid, hypophosphorous acid, methanesulfonic acid, para-toluenesulfonic acid, trifluoromethanesulfonic acid and acidic ion exchange resins. The acetalization reaction will usually be carried out at a temperature $(T_2)$ of from 70° C. to 130° C., under a vacuum of from $300 \times 10^2$ to $20 \times 10^2$ Pa (300 to 20 mbar).

When the polyol of formula (I) is xylitol or sorbitol, the temperature $(T_1)$ is greater than or equal to 95° C. and less than or equal to 130° C. and more particularly greater than or equal to 95° C. and less than or equal to 115° C., whereas the temperature $(T_2)$ is greater than or equal to 95° C. and less than or equal to 130° C. and more particularly greater than or equal to 105° C. and less than or equal to 120° C.

When the polyol of formula (I) is erythritol, the temperatures $(T_1)$ and $(T_2)$, which may be identical or different, are greater than or equal to 120° C. and less than or equal to 135° C. and more particularly less than or equal to 130° C.

Step $(a_2)$ of the process as previously defined can be supplemented, if necessary or if desired, with subsequent operations of neutralization, for example with sodium hydroxide or potassium hydroxide, and/or of filtration, and/or of decoloration, and/or of elimination of the residual polyol, for example by selective extraction by means of suitable solvent medium.

During a second step (b2), a compound of formula (III) or a mixture of compounds of formula (III) is added to the product of the reaction obtained during step (a2), by means of a stirring system which makes it possible to achieve a homogeneous composition.

The anhydride of the compound of formula (I) is formed during step (a2) of the process as a by-product resulting from the dehydration of the polyol of formula (I) in an acid medium resulting in the formation of cyclic derivatives of said polyol of formula (I).

When the polyol of formula (I) is erythritol (n=2), it dehydrates in an acid medium to 3,4-dihydroxytetrahydrofuran of formula $(B_{11})$:

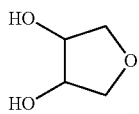

(B11)

When the polyol of formula (I) is xylitol (n=3), it dehydrates in an acid medium to 3,4-dihydroxy-2-(hydroxymethyl)tetrahydrofuran of formula ($B_{12}$) (or 1,4-anhydroxylitol):

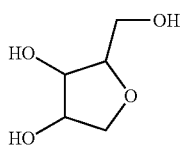

(B12)

When the polyol of formula (I) is sorbitol (n=4), it dehydrates in an acid medium to 2-(1,2-dihydroxyethyl)-3,4-dihydroxytetrahydrofuran of formula ($B_{13}$) (or 1,4-anhydrosorbitol) and to 1,5-dioxabicyclo[3.3.0]octane-3,7-diol of formula ($B_{14}$) (or isosorbide):

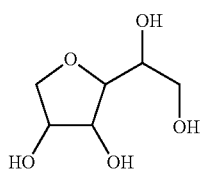

(B13)

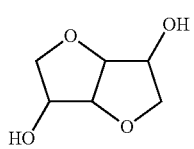

(B14)

If necessary, a third step ($c_2$) consists in adding anhydride of the compound of formula (I), and in continuing the stirring until a homogeneous composition is obtained.

A third synthesis route for the composition ($C_1$) which is a subject of the invention consists, during a first step ($a_3$), in preparing butylglycoside by reaction between butanol and glucose in the presence of an acid catalytic system, at a temperature of between 90° C. and 105° C., under partial vacuum, with concomitant elimination of the water formed during the reaction; the acid catalytic system used may be identical to that previously mentioned for the second synthesis route. Then, during a second step ($b_3$), the polyol of formula (I) is added to the reaction medium obtained at the end of step ($a_3$), with discharge by vacuum distillation of the residual butanol, of the butanol formed during the transacetalization reaction, and of the water possibly generated during the intramolecular rearrangement of said polyol; and if necessary, a third step ($c_3$) consists in adding anhydride of the compound of formula (I), and in pursuing the stirring until a homogeneous composition is obtained.

During a subsequent step ($d_3$), a compound of formula (III) or a mixture of compounds of formula (III) is added to the reaction product obtained during step ($b_3$) or with the product obtained at the end of the third step ($c_3$), by means of a stirring system which makes it possible to achieve a homogeneous composition.

The compositions ($C_1$) as previously defined can be incorporated into any type of composition for topical use (C), as previously defined, which may be cosmetic, dermocosmetic, dermopharmaceutical or pharmaceutical, intended for topical use, or else into any type of support intended to be brought into contact with the skin (paper, wipe, textile, transdermal device, etc.).

The composition for topical use (C), as previously defined, into which the compositions (C1) which are a subject of the present invention are incorporated, and which is used in the process for short-term improvement of the moisturization state of the stratum corneum of human skin epidermis, which is a subject of the present invention, is in particular in the form of an aqueous or oily solution, of an emulsion or a microemulsion of the water-in-oil (W/O) or oil-in-water (O/W) type, or a multiple emulsion of water-in-oil-in-water (W/O/W) or oil-in-water-in-oil (O/W/O) type, of a gel, of a soap or a syndet, of a balm, of a hydrodispersion, of a cream, of a foam, of an aerosol or else in an anhydrous form such as a powder.

Said composition for topical use (C) can be used as a cream, as a milk, as a bubble bath, as a shampoo, as a conditioner or as a lotion for caring for or protecting the face, the hands and the body, for instance for its short-term moisturizing effect on the epidermis after prolonged exposure to low temperatures, after prolonged exposure to solar radiation; for its short-term moisturizing effect for preventing or slowing down the appearance of the external signs of aging of human skin, such as through the appearance of wrinkles, fine lines, a modification of the microrelief, lack of elasticity and/or of tone, lack of density and/or of firmness of human skin; for its short-term moisturizing effect after shaving the face; for its short-term moisturizing effect during cleansing and/or treatment of the scalp.

In general, the compositions for topical use (C), used in the process which is the subject of the present invention, also comprise excipients and/or active ingredients that are normally used in the field of formulations for topical use, in particular cosmetic, dermocosmetic, pharmaceutical or dermopharmaceutical formulations for topical use, such as foaming and/or detergent surfactants, thickening and/or gelling surfactants, thickeners and/or gelling agents, stabilizers, film-forming compounds, solvents and cosolvents, hydrotropic agents, plasticizers, fats, oils and waxes, emulsifiers and co-emulsifiers, opacifiers, pearlescent agents, overfatting agents, sequestrants, chelating agents, antioxidants, fragrances, essential oils, preservatives, conditioning agents, whitening agents intended for bleaching body hair and the skin, active ingredients intended to provide a treating and/or protective action with respect to the skin or the hair, sunscreens, mineral fillers or pigments, particles which provide a visual effect or which are intended for encapsulating active agents, exfoliant particles, texturing agents, optical brighteners, and insect repellents.

As examples of foaming and/or detergent surfactants, optionally present in the composition for topical use (C), used in the process according to the invention, mention may be made of the topically acceptable anionic, cationic, amphoteric or nonionic foaming and/or detergent surfactants normally used in this field of activity.

Among the foaming and/or detergent anionic surfactants that can be combined with the composition for topical use (C), used in the process according to the invention, mention may be made of alkali metal salts, alkaline-earth metal salts, ammonium salts, amine salts, amino alcohol salts of alkyl ether sulfates, alkyl sulfates, alkylamido ether sulfates, alkylaryl polyether sulfates, monoglyceride sulfates, alpha-olefin sulfonates, paraffin sulfonates, alkyl phosphates, alkyl ether phosphates, alkyl sulfonates, alkylamide sulfonates, alkylaryl sulfonates, alkyl carboxylates, alkyl sulfosuccinates, alkyl ether sulfosuccinates, alkylamide sulfosuccinates, alkyl sulfoacetals, alkyl sarcosinates, acylisothionates, N-acyltaurates, acyllactylates, N-acylated derivatives of amino acids, N-acylated derivatives of peptides, N-acylated derivatives of proteins, or of fatty acids.

Among the foaming and/or detergent amphoteric surfactants that can be combined with the composition for topical use (C), used in the process according to the invention, mention may be made of alkyl betaines, alkylamido betaines, sultaines, alkylamidoalkyl sulfobetaines, imidazoline derivatives, phosphobetaines, amphopolyacetates and amphopropionates.

Among the foaming and/or detergent cationic surfactants that can be combined with the composition for topical use (C), used in the process according to the invention, mention may particularly be made of quaternary ammonium derivatives.

Among the foaming and/or detergent nonionic surfactants that can be combined with the composition for topical use (C), used in the process according to the invention, mention may more particularly be made of alkyl polyglycosides, castor oil derivatives, polysorbates, coconut amides and N-alkylamines.

Among the foaming and/or detergent nonionic surfactants that can be combined with the composition for topical use (C), used in the process according to the invention, mention may more particularly be made of the composition ($C_3$) or a mixture of compositions ($C_3$), said composition ($C_3$) being represented by the formula (IV):

$$R_2\text{—O-}(G_2)_p\text{-H} \tag{IV}$$

wherein $R_2$ represents a linear or branched, saturated or unsaturated aliphatic radical comprising from 8 to 16 carbon atoms, $G_2$ represents the residue of a reducing sugar and p represents a decimal number greater than or equal to 1.05 and less than or equal to 5, said composition ($C_3$) consisting essentially of a mixture of compounds represented by formulae ($IV_1$), ($IV_2$), ($IV_3$), ($IV_4$) and ($IV_5$):

$$R_2\text{—O-}(G_2)_1\text{-H} \tag{$IV_1$}$$

$$R_2\text{—O-}(G_2)_2\text{-H} \tag{$IV_2$}$$

$$R_2\text{—O-}(G_2)_3\text{-H} \tag{$IV_3$}$$

$$R_2\text{—O-}(G_2)_4\text{-H} \tag{$IV_4$}$$

$$R_2\text{—O-}(G_2)_5\text{-H} \tag{$IV_5$}$$

in the respective molar proportions $a_1$, $a_2$, $a_3$, $a_4$ and $a_5$, such that the sum $a_1+a_2+a_3+a_4+a_5$ is equal to 1 and that the sum $a_1+2a_2+3a_3+4a_4+5a_5$ is equal to p.

As examples of thickening and/or gelling surfactants optionally present in the composition for topical use (C), used in the process according to the invention, mention may be made of optionally alkoxylated alkyl polyglycoside fatty esters, and most particularly ethoxylated methyl polyglucoside esters, such as the PEG 120 methyl glucose trioleate or the PEG 120 methyl glucose dioleate sold respectively under the name Glucamate™ LT and Glumate™ DOE 120; alkoxylated fatty esters, such as the PEG 150 pentaerythrytyl tetrastearate sold under the name Crothix™ DS53, or the PEG 55 propylene glycol oleate sold under the name Antil™ 141; fatty-chain polyalkylene glycol carbamates, such as the PPG 14 laureth isophoryl dicarbamate sold under the name Elfacos™ T211, or the PPG 14 palmeth 60 hexyl dicarbamate sold under the name Elfacos™ GT2125.

As examples of emulsifying surfactants optionally present in the composition for topical use (C), used in the process according to the invention, mention may be made of nonionic surfactants, anionic surfactants and cationic surfactants.

As examples of emulsifying nonionic surfactants optionally present in the composition for topical use (C), used in the process according to the invention, mention may be made of fatty acid esters of sorbitol, for example Montane™ 80, Montane™ 85 and Montane™ 60; alkyl polyglycosides and compositions of alkyl polyglycosides and of linear or branched, saturated or unsaturated fatty alcohols, the alkyl chain of said alkyl polyglycosides consisting of linear or branched, saturated or unsaturated alkyl groups comprising from 14 to 22 carbon atoms, for example Montanov™, Easynov™ and Fluidanov™; fatty acid esters of polyglycerol, for example Isolan™ GI34 and Plurol™ Diisostearique; ethoxylated castor oil and ethoxylated hydrogenated castor oil, Simulsol™ 989; compositions comprising glyceryl stearate and ethoxylated stearic acid comprising between 5 mol and 150 mol of ethylene oxide, for example the composition comprising ethoxylated stearic acid comprising 135 mol of ethylene oxide and glyceryl stearate sold under the name Simulsol™ 165; polyhydroxystearates of polyglycol or of polyglycerol, for example Hypermer™ B246, Arlacel™ P135, Dehymuls™ PGPH or Decaglyn™ SHS; polyethylene glycol/alkyl glycol copolymers, for instance PEG-45 dodecylglycol copolymer, such as Elfacos™ ST 9; ethoxylated sorbitan esters, for example Montanox™; mannitan esters; ethoxylated mannitan esters; sucrose esters; methylglucoside esters.

As examples of emulsifying anionic surfactants optionally present in the composition for topical use (C), used in the process according to the invention, mention may be made of decyl phosphate, the cetyl phosphate sold under the name Amphisol™, glyceryl stearate citrate; cetearyl sulfate; the composition of arachidyl/behenyl phosphates and arachidyl/behenyl alcohols sold under the name Sensanov™ WR; soaps, for instance sodium stearate or triethanolammonium stearate, N-acylated derivatives of salified amino acids, for instance stearoyl glutamate.

As examples of emulsifying cationic surfactants optionally present in the composition for topical use (C), used in the process according to the invention, mention may be made of amine oxides, Quaternium™ 82 and the surfactants described in the International application published under number WO 96/00719 and mainly those of which the fatty chain comprises at least 16 carbon atoms.

As examples of opacifiers and/or pearlescent agents optionally present in the composition for topical use (C), used in the process according to the invention, mention may be made of sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate, and fatty alcohols comprising from 12 to 22 carbon atoms.

As examples of texturing agents optionally present in the composition for topical use (C), used in the process according to the invention, mention may be made of N-acylated derivatives of amino acids, for example the lauroyl lysine sold under the name Aminohope™ LL, the octenyl starch succinate sold under the name Dryflo™ the myristyl polyglucoside sold under the name Montanov™ 14, cellulose fibers, cotton fibers, chitosan fibers, talc, sericite and mica.

As examples of solvents and cosolvents optionally present in the composition for topical use (C), used in the process according to the invention, mention may be made of water, ethylene glycol, propylene glycol, butylene glycol, hexylene glycol, diethylene glycol, water-soluble alcohols such as ethanol, isopropanol or butanol, and mixtures of water and of said solvents.

As examples of oils optionally present in the composition for topical use (C), used in the process according to the invention, mention may be made of mineral oils such as paraffin oil, liquid petroleum jelly, isoparaffins or white mineral oils; oils of animal origin, such as squalene or squalane; vegetable oils, such as phytosqualane, sweet almond oil, coconut oil, castor oil, jojoba oil, olive oil, rapeseed oil, peanut oil, sunflower oil, wheatgerm oil, corngerm oil, soybean oil, cottonseed oil, alfalfa oil, poppyseed oil, pumpkin oil, evening primrose oil, millet oil, barley oil, rye oil, safflower oil, candlenut oil, passion flower oil, hazelnut oil, palm oil, shea butter, apricot kernel oil, beauty leaf oil, sisymbrium oil, avocado oil, calendula oil, oils derived from flowers or from vegetables; ethoxylated vegetable oils; synthetic oils, for instance fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, lanolic acid-derived esters, such as isopropyl lanolate, isocetyl lanolate, fatty acid monoglycerides, diglycerides and triglycerides, such as glyceryl triheptanoate, alkyl benzoates, hydrogenated oils, poly(alpha-olefin)s, polyolefins, such as poly(isobutane), synthetic isoalkanes, such as isohexadecane or isododecane, perfluoro oils; silicone oils, such as dimethylpolysiloxanes, methylphenylpolysiloxanes, silicones modified with amines, silicones modified with fatty acids, silicones modified with alcohols, silicones modified with alcohols and fatty acids, silicones modified with polyether groups, epoxy-modified silicones, silicones modified with fluoro groups, cyclic silicones and silicones modified with alkyl groups. In the present application, the term "oils" is intended to mean compounds and/or mixtures of compounds which are insoluble in water and which have a liquid aspect at a temperature of 25° C.

As examples of waxes optionally present in the composition for topical use (C), used in the process according to the invention, mention may be made of beeswax, carnauba wax, candelilla wax, ouricury wax, Japan wax, cork fiber wax, sugarcane wax, paraffin waxes, lignite waxes, microcrystalline waxes, lanolin waxes; ozokerite; polyethylene wax; silicone waxes; vegetable waxes; fatty alcohols and fatty acids which are solid at ambient temperature; glycerides which are solid at ambient temperature. In the present application, the term "waxes" is intended to mean compounds and/or mixtures of compounds which are insoluble in water and which have a solid aspect at a temperature greater than or equal to 45° C.

As examples of fats optionally present in the composition for topical use (C), used in the process according to the invention, mention may be made of linear or branched, saturated or unsaturated fatty alcohols comprising from 8 to 36 carbon atoms, or linear or branched, saturated or unsaturated fatty acids comprising from 8 to 36 carbon atoms.

As examples of thickeners and/or gelling agents that can be combined with the composition for topical use (C), used in the process according to the invention, mention may be made of linear or branched or crosslinked polymers of polyelectrolyte type, for instance partial or totally salified acrylic acid homopolymer, partially or totally salified methacrylic acid homopolymer, partially or totally salified 2-methyl-[(1-oxo-2-propenyl)amino]-1-propanesulfonic acid (AMPS), copolymers of acrylic acid and of AMPS, copolymers of acrylamide and of AMPS, copolymers of vinylpyrrolidone and of AMPS, copolymers of AMPS and of (2-hydroxyethyl) acrylate, copolymers of AMPS and of (2-hydroxyethyl) methacrylate, copolymers of AMPS and of hydroxyethylacrylamide, copolymers of AMPS and of N,N-dimethylacrylamide, copolymers of AMPS and of tris(hydroxyl-methyl)acrylamidomethane (THAM), copolymers of acrylic or methacrylic acid and of (2-hydroxyethyl) acrylate, copolymers of acrylic or methacrylic acid and of (2-hydroxyethyl) methacrylate, copolymers of acrylic or methacrylic acid and of hydroxyethylacrylamide, copolymers of acrylic or methacrylic acid and of THAM, copolymers of acrylic or methacrylic acid and of N,N-dimethylacrylamide, terpolymers of acrylic or methacrylic acid, of AMPS and of (2-hydroxyethyl) acrylate, terpolymers of acrylic or methacrylic acid, of AMPS and of (2-hydroxyethyl) methacrylate, terpolymers of acrylic or methacrylic acid, of AMPS and of THAM, terpolymers of acrylic or methacrylic acid, of AMPS and of N,N-dimethylacrylamide, terpolymers of acrylic or methacrylic acid, of AMPS and of acrylamide, copolymers of acrylic acid or methacrylic acid and of alkyl acrylates of which the carbon-based chain comprises between four and thirty carbon atoms, and more particularly between ten and thirty carbon atoms, copolymers of AMPS and of alkyl acrylates of which the carbon-based chain comprises between four and thirty carbon atoms and more particularly between ten and thirty carbon atoms, linear, branched or crosslinked terpolymers of at least one monomer having a free, partially salified or totally salified strong acid function, with at least one neutral monomer, and at least one monomer of formula (V):

$$CH_2=C(R7)\text{-}C(=O)\text{-}[CH_2\text{-}CH_2\text{-}O]_z\text{-}R8 \qquad (V)$$

wherein R7 represents a hydrogen atom or a methyl radical, R8 represents a linear or branched alkyl radical comprising from eight to thirty carbon atoms and z represents a number greater than or equal to one and less than or equal to fifty.

The linear or branched or crosslinked polymers of polyelectrolyte type that can be combined with the composition for topical use (C), used in the process according to the invention, may be in the form of a solution, an aqueous suspension, a water-in-oil emulsion, an oil-in-water emulsion or a powder. The linear or branched or crosslinked polymers of polyelectrolyte type that can be combined with the composition for topical use (C), used in the process according to the invention, can be selected from the products sold under the names Simulgel™ EG, Simulgel™ EPG, Sepigel™ 305, Simulgel™ 600, Simulgel™ NS, Simulgel™ INS 100, Simulgel™ FL, Simulgel™ A, Simulgel™ SMS 88, Sepinov™ EMT 10, Sepiplus™ 400, Sepiplus™ 265, Sepiplus™ S, Sepimax™ Zen, Aristoflex™ AVC, Aristoflex™ AVS, Novemer™ EC-1, Novemer™ EC-2, Aristoflex™ HMB, Cosmedia™ SP, Flocare™ ET 25, Flocare™ ET 75, Flocare™ ET 26, Flocare™ ET 30, Flocare™ ET 58, Flocare™ PSD 30, Viscolam™ AT 64 and Viscolam™ AT 100.

As examples of thickeners and/or gelling agents that can be combined with the composition for topical use (C), used in the process according to the invention, mention may be made of polysaccharides consisting only of monosaccharides, such as glucans or glucose homopolymers, glucomannoglucans, xyloglycans, galactomannans of which the degree of substitution (DS) of the D-galactose units on the main chain of D-mannose is between 0 and 1, and more particularly between 1 and 0.25, such as galactomannans originating from cassia gum (DS=1/5), from locust bean gum (DS=1/4), from tara gum (DS=1/3), from guar gum (DS=1/2) or from fenugreek gum (DS=1).

As examples of thickeners and/or gelling agents that can be combined with the compositions (C) for topical use, which can be used in a process for short-term improvement of the moisturization state of the stratum corneum of human skin epidermis, mention may be made of polysaccharides consisting of monosaccharide derivatives, such as sulfated galactans and more particularly carrageenans and agar, uronans and more particularly aligns, alginates and pectins, heteropolymers of monosaccharides and of uronic acids and more particularly xanthan gum, gellan gum, exudates of gum Arabic and of karaya gum, and glucoseaminoglycans.

As examples of thickeners and/or gelling agents that can be combined in the composition for topical use (C), used in the process according to the invention, mention may be made of cellulose, cellulose derivatives such as methylcellulose, ethylcellulose or hydroxypropylcellulose, silicates, starch, hydrophilic starch derivatives, and polyurethanes.

As examples of stabilizers that can be combined with the composition for topical use (C), used in the process according to the invention, mention may be made of microcrystalline waxes, and more particularly ozokerite, mineral salts such as sodium chloride and magnesium chloride, and silicone polymers such as polysiloxane polyalkyl polyether copolymers.

As examples of spring or mineral waters that can be combined with the composition for topical use (C), used in the process according to the invention, mention may be made of spring or mineral waters having a mineralization of at least 300 mg/l, in particular Avene water, Vittel water, waters from the Vichy basin, Uriage water, Roche Posay water, Bourboule water, Enghien-les-bains water, Saint-Gervais-les-bains water, Néris-les-bains water, Allevard-les-bains water, Digne water, Maizieres water, Neyrac-les-bains water, Lons le Saunier water, Rochefort water, Saint Christau water, Fumades water and Tercis-les-bains water.

As examples of hydrotropic agents that can be combined with the composition for topical use (C), used in the process according to the invention, mention may be made of xylene sulfonates, cumen sulfonates, hexylpolyglucoside, 2-ethylhexylpolyglucoside and n-heptylpolyglucoside.

As examples of deodorizing agents that can be combined with the composition for topical use (C), used in the process according to the invention, mention may be made of alkali metal silicates, zinc salts such as zinc sulfate, zinc gluconate, zinc chloride or zinc lactate; quaternary ammonium salts such as cetyltrimethylammonium salts, cetylpyridinium salts; glycerol derivatives such as glyceryl caprate, glyceryl caprylate, polyglyceryl caprate; 1,2-decanediol; 1,3-propanediol; salicylic acid; sodium bicarbonate; cyclodextrins; metal zeolites; Triclosan™; aluminum bromohydrate, aluminum chlorohydrates, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octochlorohydrate, aluminum sulfate, sodium aluminum lactate, complexes of aluminum chlorohydrate and glycol, such as the complex of aluminum chlorohydrate and of propylene glycol, the complex of aluminum dichlorohydrate and of propylene glycol, the complex of aluminum sesquichlorohydrate and of propylene glycol, the complex of aluminum chlorohydrate and of polyethylene glycol, the complex of aluminum dichlorohydrate and of polyethylene glycol, and the complex of aluminum sesquichlorohydrate and of polyethylene glycol.

As examples of sunscreens that can be combined with the composition for topical use (C), used in the process according to the invention, mention may be made of all those which appear in the modified cosmetics directive 76/768/EEC annex VII.

Among the organic sunscreens that can be combined with the composition for topical use (C) used in the process according to the invention, mention may be made of the family of benzoic acid derivatives, for instance para-aminobenzoic acids (PABAs), in particular monoglyceryl esters of PABA, ethyl esters of N,N-propoxy PABA, ethyl esters of N,N-diethoxy PABA, ethyl esters of N,N-dimethyl PABA, methyl esters of N,N-dimethyl PABA, butyl esters of N,N-dimethyl PABA; the family of anthranilic acid derivatives, for instance homomenthyl-N-acetyl anthranilate; the family of salicylic acid derivatives, for instance amyl salicylate, homomenthyl salicylate, ethylhexyl salicylate, phenyl salicylate, benzyl salicylate, or p-isopropanolphenyl salicylate; the family of cinnamic acid derivatives, for instance ethylhexyl cinnamate, ethyl 4-isopropylcinnamate, methyl 2,5-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, mono(2-ethylhexanoyl)glyceryl di(para-methoxycinnamate); the family of benzophenone derivatives, for instance 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octyloxybenzophenone, 4-hydroxy-3-carboxybenzophenone; 3-(4'-methylbenzylidene)-d,l-camphor, 3-(benzylidene)-d,l-camphor, camphor benzalkonium methosulfate; urocanic acid, ethyl urocanate; the family of sulfonic acid derivatives, for instance 2-phenylbenzimidazole-5 sulfonic acid and salts thereof; the family of triazine derivatives, for instance hydroxyphenyl triazine, ethylhexyloxyhydroxyphenyl-4-methoxyphenyltriazine, 2,4,6-trianillino-(p-carbo-2'-ethylhexyl-1'-oxy)-1,3,5-triazine, benzoic acid 4,4-((6-(((1,1-dimethylethyl)amino) carbonyl)phenyl)amino)-1,3,5-triazine-2,4-diyl diimino) bis (2-ethylhexyl) ester, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methyphenyl) benzotriazole; dibenzazine; dianisoylmethane, 4-methoxy-4"-t-butylbenzoylmethane; 5-(3,3-dimethyl-2-norbornylidene)-3-pentan-2-one; the family of diphenyl acrylate derivatives, for instance 2-ethylhexyl-2-cyano-3,3-diphenyl-2-propenoate, ethyl-2-cyano-3,3-diphenyl-2-propenoate; the family of polysiloxanes, for instance benzylidene siloxane malonate.

Among the inorganic sunscreens, also known as "mineral screens", that can be combined with the composition for topical use (C), used in the process according to the invention, mention may be made of titanium oxides, zinc oxides, cerium oxide, zirconium oxide, yellow, red or black iron oxides, and chromium oxides. These mineral screens may or may not be micronized, may or may not have undergone surface treatments and may be optionally present in the form of aqueous or oily predispersions.

As examples of active ingredients that can be combined with the composition for topical use (C), used in the process according to the invention, mention may be made of vitamins and derivatives thereof, in particular esters thereof, such as retinol (vitamin A) and esters thereof (retinyl palmitate for example), ascorbic acid (vitamin C) and esters thereof, sugar derivatives of ascorbic acid (for instance ascorbyl glucoside), tocopherol (vitamin E) and esters thereof (for instance tocopheryl acetate), vitamin B3 or B10 (niacinamide and derivatives thereof); compounds showing a skin-lightening or -depigmenting action, for instance the ω-undecelynoyl phenylalanine sold under the name Sepiwhite™MSH, Sepicalm™VG, the glycerol monoester and/or diester of ω-undecelynoyl phenylalanine, ω-undecelynoyl dipeptides, arbutin, kojic acid, hydroquinone; compounds showing a soothing action, in particular Sepicalm™ S, allantoin and bisabolol; anti-inflammatories; compounds showing a moisturizing action, such as urea, hydroxyureas, glycerolglucoside, diglycerolglucoside, polyglycerylglucosides; polyphenol-rich plant extracts, for instance grape extracts, pine extracts, wine extracts, olive extracts; compounds showing a slimming or lipolytic action, for instance caffeine or derivatives thereof, Adiposlim™, Adipoless™, fucoxanthine; N-acylated proteins; N-acylated peptides, for instance Matrixil™; N-acylated amino acids; partial hydrolyzates of N-acylated proteins; amino acids; peptides; total protein hydrolyzates; soybean extracts, for example Raffermine™; wheat extracts, for example Tensine™ or Gliadine™; plant extracts, such as tannin-rich plant extracts, isoflavone-rich plant extracts or terpene-rich plant extracts; extracts of freshwater or seawater algae; marine plant extracts; marine extracts in general, such as corals; essential waxes; bacterial extracts; ceramides; phospholipids; compounds showing an antimicrobial action or a purifying action, for instance Lipacide™ C8G, Lipacide™ UG, Sepicontrol™ A5; Octopirox™ or Sensiva™ SC50; compounds showing an energizing or stimulating property, for instance Physiogenyl™, panthenol and derivatives thereof, for instance Sepicap™ MP; anti-aging active agents, for instance Sepilift™ DPHP, Lipacide™ PVB, Sepivinol™, Sepivital™, Manoliva™, Phyto-Age™, Timecode™; Survicode™; anti-photoaging active agents; agents for protecting the integrity of the dermoepidermal junction; agents for increasing the synthesis of extracellular matrix components such as collagen, elastins, glycosaminoglycans; active agents which act favorably on chemical cell communication, for instance cytokines, or physical cell communication, for instance integrins; active agents which create a "heating" sensation on the skin, for instance skin microcirculation activators (for instance nicotinic acid derivatives) or products which create a feeling of "freshness" on the skin (for instance menthol and derivatives); active agents for improving skin microcirculation, for example veinotonics; draining active agents; active agents for decongestive purposes, for instance extracts of ginko biloba, of ivy, of horse chestnut, of bamboo, of ruscus, of butcher's broom, of *Centalla asiatica*, of fucus, of rosemary, of willow; agents for tanning or browning the skin, for instance dihydroxyacetone (DHA), erythrulose, mesotartric aldehyde, glutaraldehyde, glyceraldehyde, alloxane, ninhydrin, plant extracts, for instance extracts of redwood of the genus *Pterocarpus* and of the genus *Baphia*, such as *Pteropcarpus santalinus, Pterocarpus osun, Pterocarpus soyauxii, Pterocarpus erinaceus, Pterocarpus indicus* or *Baphia nitida*, such as those described in European patent application EP 0 971 683; agents known for their action of facilitating and/or accelerating tanning and/or browning of human skin, and/or for their action of coloring human skin, for instance carotenoids (and more particularly beta-carotene and gamma-carotene), the product sold under the trade name "Carrot oil" (INCI name: Daucus Carota, *Helianthus annuus* Sunflower oil) by the company Provital, which contains carotenoids, vitamin E and vitamin K; tyrosine and/or derivatives thereof, known for their effect on accelerating tanning of human skin in combination with exposure to ultraviolet radiation, for instance the product sold under the trade name "SunTan Accelerator™" by the company Provital, which contains tyrosine and riboflavins (vitamin B), the complex of tyrosine and of tyrosinase sold under the trade name "Zymo Tan Complex" by the company Zymo Line, the product sold under the trade name MelanoBronze™ (INCI name: Acetyl Tyrosine, Monk's pepper extract (Vitex Agnus-castus)) by the company Mibelle, which contains acetyl tyrosine, the product sold under the trade name Unipertan VEG-24/242/2002 (INCI name: butylene glycol and Acetyl Tyrosine and hydrolyzed vegetable protein and Adenosine triphosphate) by the company Unipex, the product sold under the trade name "Try-Excell™" (INCI name: Oleoyl Tyrosine and *Luffa Cylindrica* (Seed) Oil and Oleic acid) by the company Sederma, which contains marrow seed extracts (or sponge gourd oil), the product sold under the trade name "Actibronze™" (INCI name: hydrolyzed wheat protein and acetyl tyrosine and copper gluconate) by the company Alban Muller, the product sold under the trade name Tyrostan™ (INCI name: potassium caproyl tyrosine) by the company Synerga, the product sold under the trade name Tyrosinol (INCI name: Sorbitan Isostearate, glyceryl oleate, caproyl Tyrosine) by the company Synerga, the product sold under the trade name InstaBronze™ (INCI name: Dihydroxyacetone and acetyl tyrosine and copper gluconate) sold by the company Alban Muller, the product sold under the trade name Tyrosilane (INCI name: methylsilanol and acetyl tyrosine) by the company Exymol; peptides known for their melanogenesis-activating effect, for instance the product sold under the trade name Bronzing SF Peptide powder (INCI name: Dextran and Octapeptide-5) by the company Infinitec Activos, the product sold under the trade name Melitane (INCI name: Glycerin and Aqua and Dextran and Acetyl hexapeptide-1) comprising acetyl hexapeptide-1 known for its alpha-MSH agonist action, the product sold under the trade name Melatimes Solutions™ (INCI name: Butylene glycol, Palmitoyl Tripeptide-40) by the company Lipotec, sugars and sugar derivatives, for instance the product sold under the trade name Tanositol™ (INCI name: inositol) by the company Provital, the product sold under the trade name Thalitan™ (or Phycosaccharide™ AG) by the company Codif International (INCI name: Aqua and hydrolyzed algin (*Laminaria Digitata*) and magnesium sulfate and manganese sulfate) containing an oligosaccharide of marine origin (guluronic acid and mannuronic acid chelated with magnesium ions and manganese ions), the product sold under the trade name Melactiva™ (INCI name: Maltodextrin, *Mucuna Pruriens* Seed extract) by the company Alban Muller, flavonoid-rich compounds, for instance the product sold under the trade name "Biotannin" (INCI name: Hydrolyzed citrus *Aurantium dulcis* fruit extract) by the company Silab and known to be rich in lemon flavonoids (of hesperidine type).

As examples of antioxidants that can be combined with the composition for topical use (C), used in the process according to the invention, mention may be made of EDTA and salts thereof, citric acid, tartaric acid, oxalic acid, BHA (butylhydroxyanisol), BHT (butylhydroxytoluene), tocopherol derivatives, such as tocopheryl acetate, mixtures of antioxidant compounds such as Dissolvine™ GL 47S sold by the company Akzo Nobel under the INCI name: Tetrasodium Glutamate Diacetate.

A subject of the invention is also a composition ($C_1$) as previously defined, for use thereof in a therapeutic treatment intended to decrease and/or eliminate and/or prevent chapping and/or dry patches and/or cracks and/or atopic dermatitis and/or ichtyosis and/or states of dryness of the skin or of the mucous membranes, accompanying cutaneous and/or mucosal pathological conditions such as eczema.

The composition ($C_1$) for use thereof in a therapeutic treatment as previously defined can be combined with pharmaceutical, in particular dermatological, active ingredients.

The following examples illustrate the invention without however limiting it.

A) EXAMPLE OF PREPARATION OF A COMPOSITION ($C_{1A}$) ACCORDING TO THE INVENTION BASED ON XYLITOL, ON ANHYDROXYLITOL, ON XYLITYL POLYGLUCOSIDE AND ON GLYCEROL 703.0 grams of xylitol, i.e. one mole equivalent, are introduced into a jacketed glass reactor, in which a heat-exchange fluid circulates, and which is equipped with an efficient stirrer. The xylitol is melted at a temperature of 135° C., and the resulting viscous paste is cooled to 115° C. 210.9 grams of glucose, i.e. 0.3 molar equivalent, are then gradually added to the reaction medium in order to enable its homogeneous dispersion. An acid catalytic system consisting of 1.29 grams of sulfuric acid at 96% is added to the resulting mixture. The reaction medium is placed under a partial vacuum of from $90 \times 10^2$ Pa (90 mbar) to $45 \times 10^2$ Pa (45 mbar) and maintained at a temperature of 100° C.-105° C. for a period of 4 h 30 with discharge of the water formed, by means of a distillation assembly. The reaction medium is then cooled to 95° C.-100° C. and neutralized by adding 5 g of 30% sodium hydroxide, so as to bring the pH of a solution containing 1% of this mixture to a value of 5.0.

The composition ($C_{2A}$) is thus obtained, and is analyzed in order to determine the weight content of the various compounds of which it is constituted, by means of a gas chromatograph, equipped with a metallic column HT-SIM-DIST™ CB (PE Chropack™) 10 m×0.53 mm ID-film thickness at 0.5 μm, with helium as vector gas, and equipped with an FID-type detector. The composition ($C_{2A}$) thus comprises, for 100% of the weight thereof:
  18.7% by weight of xylitol,
  37.6% by weight of 1,4-anhydroxylitol corresponding to formula ($B_{12}$),
  43.7% by weight of xylityl glucosides, characterized by a degree of polymerization x equal to 1.21, residual glucose: less than 0.1% by weight.

15.0 grams of the composition ($C_{2A}$) previously obtained and 30 grams of glycerol are mixed at a temperature of 45° C. in a jacketed glass reactor, in which a heat exchange fluid circulates, and which is equipped with an efficient stirrer. After obtaining a homogeneous mixture, a composition ($C_{1A}$) is obtained which comprises, for 100% of the weight thereof:
  6.3% by weight of xylitol,
  12.5% by weight of 1,4-anhydroxylitol corresponding to formula ($B_{12}$),
  14.6% by weight of xylityl glucosides, characterized by a degree of polymerization x equal to 1.21,
  66.6% by weight of glycerol.

The xylityl glucosides/glycerol weight ratio is equal to 0.219.

B) EXAMPLE OF DEMONSTRATION OF THE SHORT-TERM IMPROVEMENT OF THE MOISTURIZATION STATE OF THE STRATUM CORNEUM OF HUMAN SKIN EPIDERMIS BY APPLICATION OF A COMPOSITION COMPRISING A COMPOSITION ($C_{1A}$) ACCORDING TO THE INVENTION BASED ON XYLITOL, ON ANHYDROXYLITOL, ON XYLITYL POLYGLUCOSIDE AND ON GLYCEROL

B1)—Preparation of Compositions According to the Prior Art and According to the Invention Four compositions called ($E_1$), ($E_2$), ($E_3$) and ($E_4$), of which the weight proportions of the constituents thereof are reported in table 1, are prepared.

The composition ($E_4$) comprising the composition ($C_{1A}$) represents a composition according to the invention, while the compositions ($E_1$), ($E_2$) and ($E_3$) represent the prior art.

The process for the preparation thereof is the following:
  the various constituents of the fatty phase (Phase B), previously melted separately, are poured into a beaker, at a temperature of 80° C., and the mixture of the fatty phases is kept stirring by means of a mechanical stirrer, equipped with a "blade"-type spindle, at a speed of 100 rpm at a temperature of 80° C. for 30 minutes;
  the Sepiplus™ 400 thickening polymer (Phase C) is then gradually added to the mixture of fatty phases at a temperature of 80° C.;
  the medium is then cooled to a temperature of 60° C., then the water (Phase A) and the moisturizing active agent (Phase D) are gradually added;
  the mixture obtained is then stirred by means of a Silverson™ homogenizer, for 4 minutes at 4000 rpm, then cooled to 25° C. for 10 minutes with stirring at 100 rpm, then to 10° C. at 100 rpm for 10 minutes with addition of the preservatives (Phase E).

TABLE 1

|  |  | ($E_1$) | ($E_2$) | ($E_3$) | ($E_4$) |
| --- | --- | --- | --- | --- | --- |
| Phase A | Water | QSP100 | QSP100 | QSP100 | QSP100 |
| Phase B: | Montanov 202[(1)] | 3% | 3% | 3% | 3% |
|  | Lanon ™ 99[(2)] | 5% | 5% | 5% | 5% |
|  | Lanol ™ 2681[(3)] | 13% | 13% | 13% | 13% |
| Phase C: | Sepiplus ™ 400[(4)] | 0.8% | 0.8% | 0.8% | 0.8% |
| Phase D | Composition ($C_{2A}$) | / | 1.5% | / | / |
|  | Glycerol | / | / | 3% | / |
|  | Composition ($C_{1A}$) | / | / | / | 4.5% |

TABLE 1-continued

|  |  | ($E_1$) | ($E_2$) | ($E_3$) | ($E_4$) |
|---|---|---|---|---|---|
| Phase E: | Euxyl ™ PE9010[5] | 1% | 1% | 1% | 1% |
|  | Sensiva ™ PA40[6] | 0.5% | 0.5% | 0.5% | 0.5% |
| Phase F: | Citric acid | QS | QS | QS | QS |
| pH adjustment |  | pH = 5.5 | pH = 5.5 | pH = 5.5 | pH = 5.5 |
| Appearance at D7 |  | Flowable white | Flowable white | Flowable white | Flowable white |
| Viscosity in mas-1 at D7 |  | M4V6 44 000 | M4V6 34 000 | M4V6 45 000 | M4V6 44 000 |
| Stability T45 at D7 |  | Stable | Stable | Stable | Stable |

[1]Montanov ™ 202: (arachidyl alcohol, behenyl alcohol and arachidyl glucoside); self-emulsifying composition such as those described in EP 0 977 626;
[2]Lanol ™ 99: isononyl isononoate;
[3]Lanol ™ 2681: coco-caprylate/caprate;
[4]Sepiplus ™ 400: self-invertible inverse latex of polyacrylates in polyisobutene and comprising polysorbate 20, as described in WO 2005/040230;
[5]Euxyl ™ PE 9010: (INCI name: Phenoxyethanol (and) Ethylhexylglycerin);
[6]Sensiva ™ PA40: (INCI name: Phenylpropanol & Propanediol & Caprylyl Glycol & Tocopherol).

B2) Demonstration of the Properties and Characteristics of the Compositions According to the Invention Compared with the Compositions of the Prior Art The compositions ($E_1$), ($E_2$), ($E_3$) and ($E_4$) are subsequently evaluated as follows:
  measurement of the degree of cutaneous moisturization after a given period of time following the application to the skin of the compositions ($E_1$), ($E_2$), ($E_3$) and ($E_4$), and comparison with the degree of cutaneous moisturization of the skin surface before the treatment of said skin surface with said compositions, and
  measurement of the insensible water loss after a given period of time following the application to the skin of the compositions ($E_1$), ($E_2$), ($E_3$) and ($E_4$), and comparison with the insensible water loss from the skin surface before the treatment of said skin surface with said compositions.

A tested composition will be considered as allowing a short-term improvement of the moisturization state of the stratum corneum of human skin epidermis if, for said composition, the following are observed:
  an increase in the degree of moisturization of the stratum corneum of human skin epidermis, measured and observed within a period of between three hours and eight hours after the application of said tested composition to the surface of said stratum corneum, greater than or equal to 40% relative to the degree of moisturization measured and observed before the application of said tested composition, and
  a decrease in the insensible water loss from the human skin epidermis, measured and observed within a period of between 30 minutes and 60 minutes after the application of said composition to be tested to the surface of the human skin epidermis to be treated, less than or equal to 10% relative to the insensible water loss measured and observed before application of said tested compound.

B2.1) Demonstration of the Degree of Moisturization

B2.1.1 Principle of the Method

The degree of cutaneous moisturization is determined by evaluating the electrical properties of the skin, for instance the impedance, resistance and capacitance, since these dielectric parameters measured at the surface of said skin vary with the amount of water contained in the stratum corneum.

The principle retained and used in the context of the present patent application is based on the measurement of the variation in the dielectric capacitance of the skin surface. Indeed, just like any biological material or any biological matrix, the stratum corneum can be characterized by its mean capacitance value; this dielectric property varies with the amount of water that it contains.

B2.1.2 Material

The degree of cutaneous moisturization is measured using the corneometer model CM825™, sold by the company Courage & Khasaka, equipped with a sensor made up of two metal electrodes. When the corneometer is supplied with electricity, it makes it possible to apply an electric field through the stratum corneum and to measure the capacitance corresponding to the state of the skin to which the electric field has been applied.

B2.1.3 Experimental Protocol

The study of the moisturizing effect of the compounds to be tested was carried out on a group of twenty-five volunteers, according to a time course of measurement before the application of the compositions (t0), after a period of three hours following the application of the composition to be tested to the skin (t3h), and after a period of eight hours following the application of the composition to be tested to the skin (t8h). The characteristics of the group of volunteers are the following:
  women from 22 to 50 years old,
  with an average age of 37,
  of Caucasian type, and
  of phototype I to IV.

The measurements were carried out in intra-individual mode, that is to say that each subject is its own control. For each volunteer of the group, the following skin areas are defined on the outer faces of the legs:
  an area treated with the composition ($E_2$) comprising 1.5% by weight of composition ($C_{2A}$);
  an area treated with the composition ($E_3$) comprising 3% by weight of glycerol;
  an area treated with the composition ($E_4$) comprising 4.5% by weight of composition ($C_{1A}$);
  an area treated with the composition ($E_1$), placebo control;
  a nontreated control area.

In order to limit the variations caused by modifications of the environmental conditions, undesirable for the quality of the evaluation, the entire study took place in a laboratory under controlled temperature (23° C.+/−2° C.) and relative humidity (45%-55%) conditions.

After an acclimatization period of 30 minutes, the compositions to be tested are applied by a technician to the skin areas previously defined, in a proportion of 2 mg/cm² for each product.

For each volunteer and for each area defined, the degree of moisturization of the skin area is measured using the corneometer CM825™, three hours and eight hours following the application of each composition.

B2.1.4 Expression of the Results

The measurements of the degree of moisturization are expressed in arbitrary units (au). An increase in the values (expressed in au) indicates an increase in the water content of the stratum corneum, thus characterizing a moisturizing effect.

The values measured with the corneometer at each of the measurement times are recorded. At each measurement of a treated area, the nontreated control area is also measured, in order to take into account the natural variations to the skin and the impact of the variations in the environmental conditions on the measurements.

The effect of a tested composition is a variation measured on the treated area in question, corrected by the variation observed in the same period of time on the nontreated area, and expressed as percentage increase ($\Delta$) relative to the starting value measured at the time $t_0$, corresponding to the value measured before the application of the product to be tested.

The following are thus defined:

$T(t_x)$: the mean value of the degree of moisturization, expressed in arbitrary units (au), measured at the time $t_x$ (x hours after the application of the composition to be tested), on the treated area.

$T(t_0)$: the mean value of the degree of moisturization, expressed in arbitrary units (au), measured at the time $t_0$ (before the application of composition to be tested), on the treated area (initial basal value).

$NT(t_x)$: the mean value of the degree of moisturization, expressed in arbitrary units (au), measured at the time $t_x$ on the nontreated area.

$NT(t_0)$: the mean value of the degree of moisturization, expressed in arbitrary units (au), measured at the time $t_0$ on the nontreated area (initial basal value);

the percentage increase ($\Delta$) of the corrected degree of moisturization is calculated in the following way:

$$\Delta = 100 \times \{[T(t_x)-T(t_0)] - [NT(t_x)-NT(t_0)]\} / [T(t_0) + [NT(t_x) - NT(t_0)]]$$

B2.1.5 Results Obtained

The mean and non-corrected measurements of the degree of moisturization that were obtained for the application of the compositions ($E_1$), ($E_2$), ($E_3$) and ($E_4$) are indicated in table 2 below:

TABLE 2

| Time t at which the measurement is carried out | Mean degrees of moisturization measured | | |
|---|---|---|---|
| | $t = t_0$ | $t = t_3$ | $t = t_8$ |
| Nontreated control area | $NT(t_0) = 16.9$ | $NT(t_3) = 18.4$ | $NT(t_8) = 17.5$ |
| Area treated with the composition ($E_1$) | $T(t_0) = 19.5$ | $T(t_3) = 25.0$ | $T(t_8) = 22.7$ |
| Area treated with the composition ($E_2$) | $T(t_0) = 19.7$ | $T(t_3) = 25.8$ | $T(t_8) = 24.2$ |
| Area treated with the composition ($E_3$) | $T(t_0) = 19.1$ | $T(t_3) = 27.7$ | $T(t_8) = 26.3$ |
| Area treated with the composition ($E_4$) | $T(t_0) = 19.2$ | $T(t_3) = 30.3$ | $T(t_8) = 29.3$ |

The mean variations, expressed in the form of the percentage increase in the corrected degree of moisturization ($\Delta$) as previously defined, obtained for the application of the compositions ($E_1$), ($E_2$), ($E_3$) and ($E_4$), are reported in table 3 below:

TABLE 3

| Time t at which the measurement is carried out | Percentage increase in the degree of moisturization ($\Delta$) | | |
|---|---|---|---|
| | $t = t_0$ | $t = t_3$ | $t = t_8$ |
| Area treated with the composition ($E_1$) | — | ($\Delta$) = +19% | ($\Delta$) = +13% |
| Area treated with the composition ($E_2$) | — | ($\Delta$) = +21% | ($\Delta$) = +19% |
| Area treated with the composition ($E_3$) | — | ($\Delta$) = +35% | ($\Delta$) = +33% |
| Area treated with the composition ($E_4$) | — | ($\Delta$)* = +46% | ($\Delta$)** = +45% |

*p value according to the Student's test: p = 0.041 (comparison of the compositions $E_3$ and $E_4$)
**p value according to the Student's test: p = 0.078 (comparison of the compositions ($E_3$ and $E_4$)

Statistical Comparison of the Products

The statistical analysis of the results was carried out by means of a two-sided Student's test and a threshold of significance set at 5%, by comparing the compositions in pairs.

It will be considered that a difference between the efficacy of two products is:

significant if p<0.05;
said to be "at the limit of significance" if 0.05<p<0.1;
and not significant if p>0.1.

B2.1.6 Analysis of the Results

After three hours following the application of the tested compounds, the change in the mean of the degrees of moisturization measured and corrected (parameter ($\Delta$), as previously defined and expressed as %), shows that the increase in the corrected degree of moisturization is 46% for the composition ($E_4$), compared with 35% for the composition ($E_3$), compared with 21% for the composition ($E_2$) and 19% for the placebo composition ($E_1$).

After eight hours following the application of the tested compounds, the change in the mean of the degrees of moisturization measured and corrected (parameter ($\Delta$), as previously defined and expressed as %), shows that the increase in the corrected degree of moisturization is 45% for the composition ($E_4$), compared with 33% for the composition ($E_3$), compared with 19% for the composition ($E_2$) and 13% for the placebo composition ($E_1$).

As a result, the composition ($E_4$) exhibits the best short-term moisturizing properties, as previously defined, among the compositions tested.

B2.2) Demonstration of the Insensible Water Loss

B2.2.1 Principle of the Method

The insensible water loss (IWL) is a way of measuring the evaporation of water by the epidermis, and its measurement represents the passive diffusion of water through the horny layer from the inside to the outside. It is based on Fick's law of diffusion, according to which the degree of water evaporation is proportional to the water vapor pressure gradient. Two methods of measurement can be used, open-chamber or closed-chamber methods. The method used in the present experimental section is the closed-chamber method. The closed-chamber measurements are carried out with a cylindrical probe closed in its upper portion, and sometimes equipped with a condenser maintained at a controlled temperature. The detectors are located inside the cylinder. The application of the closed cylindrical probe flush with the surface of the skin makes it possible, by measuring the increase in the humidity gradient in the chamber, to determine the amount of water evaporated at the surface of the skin.

B2.2.2 Material

The insensible water loss is measured using the equipment sold under the trade name Vapometer Delfin™ SWL4436.

B2.2.3 Experimental Protocol

The study of the effect on the insensible water loss of the compositions to be tested was carried out on a group of 10 volunteers, according to a time course of measurement before the application of the compositions ($t_0$), after a period $t_x$ of 30 minutes following the application of the composition to be tested to the skin. The characteristics of the group of volunteers are the following:

women from 18 to 50 years old,
with an average age of 39,
of Caucasian type, and
of phototype I to IV.

The measurements were carried out in intra-individual mode, that is to say each subject is its own control.

For each volunteer of the group, the following skin areas are defined on the outer faces of the legs:

an area treated with the composition ($E_2$) comprising 1.5% by weight of composition ($C_{2A}$);
an area treated with the composition ($E_3$), comprising 3% by weight of glycerol;
an area treated with the composition ($E_4$) comprising 4.5% by weight of the composition ($C_{1A}$);
an area treated with the composition ($E_1$), placebo control;
a nontreated control area.

In order to limit the variations caused by modifications of the environmental conditions, undesirable for the quality of the evaluation, the entire study is carried out in a laboratory under controlled temperature (23° C.+/−2° C.) and relative humidity (45%-55%) conditions.

After an acclimatization period of 30 minutes, the compositions to be tested are applied by a technician to the skin areas previously defined, in a proportion of 2 mg/cm² for each product.

For each volunteer and for each area defined, the insensible water loss (IWL) of the skin area is measured with the vapometer Delfin™ SWL4436, 30 minutes after the application of each composition.

B2.2.4 Expression of the Results

The insensible water loss measurements carried out according to this principle and this procedure are expressed in g/m²/h.

A decrease in the insensible water loss indicates a reduction in the evaporation of water from the skin surface, therefore defining an occlusive effect, not desired for normal skin.

The values measured with the vapometer at each of the measurement times are recorded. At the same time, the nontreated control area is measured, in order to take into account the natural variations of the skin and the impact of the variations in environmental conditions on the measurements.

The effect of a tested composition is a variation measured on the treated area in question, corrected by the variation observed in the same period of time on the nontreated area, and expressed as percentage variation ($\Delta'$) relative to the starting value measured at time $t_0$, corresponding to the value measured before the application of the product to be tested. The following are thus defined:

T'($t_{30}$): the mean value of the insensible water loss (expressed in g/m²/h), measured thirty minutes after the application of the composition to be tested to the treated area;

T' ($t_0$): the mean value of the insensible water loss (expressed in g/m²/h), measured at $t_0$ on the treated area (initial basal value);

NT' ($t_{30}$): the mean value of the insensible water loss (expressed in g/m²/h) measured thirty minutes after the application of the composition to be tested;

NT'($t_0$): the mean value of the insensible water loss (expressed in g/m²/h), measured at $t_0$ on the nontreated area (initial basal value).

The weighted percentage variation of the insensible water loss ($\Delta'$) is calculated in the following way:

$$\Delta'=100\times\{[T'(t_{30})-T'(t_0)]-[NT'(t_{30})-NT'(t_0)]\}/[T'(t_0)+[NT'(t_{30})-NT'(t_0)]]$$

B2.2.5 Results Obtained

The mean and weighted measurements of the insensible water loss (IWL), expressed in the form of the weighted percentage variation of the insensible water loss ($\Delta'$), obtained for the application of the compositions ($E_1$), ($E_2$), ($E_3$) and ($E_4$), are recorded in table 4 below:

TABLE 4

| | Percentage variation of (IWL) ($\Delta'$) |
|---|---|
| Area treated with the composition (E1) | ($\Delta'$) = −2% |
| Area treated with the composition (E2) | ($\Delta'$) = −6% |
| Area treated with the composition (E3) | ($\Delta'$) = −17% |
| Area treated with the composition (E4) | ($\Delta'$) = −8% |

B2.2.6 Analysis of the Results

Thirty minutes after the application of the tested compositions, the results obtained reveal that the weighted insensible water loss is −8% for the composition ($E_4$), compared with −6% for the composition ($E_2$), compared with −17% for the composition ($E_3$) and therefore a marked occlusive effect when the skin is treated with the composition ($E_3$), which comprises 3% by weight of glycerol as moisturizing agent.

B2.3) Conclusion

The evaluation of the compositions ($E_1$), ($E_2$), ($E_3$) and ($E_4$) shows that the composition ($E_4$), comprising a composition ($C_{1A}$), allows a short-term improvement of the moisturization state of the stratum corneum of human skin epidermis.

When the results obtained for the composition ($E_1$) and for the compositions ($E_3$) and ($E_2$), comprising respectively glycerol and the composition ($C_{2A}$), are put into perspective, this clearly demonstrates that the short-term improvement in the moisturization state of the stratum corneum of human skin epidermis, obtained by using the composition ($E_4$) based on composition ($C_{1A}$) according to the invention, could not be deduced from the results associated with the prior art compositions.

C) FORMULATIONS

In the following formulae, the percentages are expressed by weight of the formulation.

C.1 Makeup Removal Fluid for the Face

| Formula | |
|---|---|
| Composition ($E_4$) | 10.00% |
| Methyl paraben | 0.15% |
| Phenoxyethanol | 0.80% |
| Sepicalm ™ S | 1.00% |
| Fragrance/Scent | 0.10% |
| Water | qs. 100.00% |

Procedure:
The various ingredients are mixed in the water with magnetic stirring in the order indicated, and the pH is adjusted to about 7.

C.2 Hair and Body Shampoo for Children

| | Formula | |
|---|---|---|
| A | Composition ($E_4$) | 15.00% |
| | Proteol ™ APL | 5.00% |
| | Sepicide ™ HB | 0.50% |
| | Fragrance/scent | 0.10% |
| B | Water | 20.00% |
| | Capigel ™ 98 | 3.50% |
| C | Water | Q.S. 100.00% |
| | Sepicide ™ CI | 0.30% |
| | Dye | Q.S. |
| | Sodium hydroxide | Q.S. pH = 7.2 |

Procedure:
The composition ($E_4$) is mixed with the Proteol™ APL and the Sepicide™ HB (Phase A). The Capigel™ 98 is diluted in a portion of the water and is added to the phase A previously obtained (Phase B). The remainder of the water is added to phase B, followed by the Sepicide™ CI and the dye. The pH of the mixture is adjusted to approximately 7.2 with sodium hydroxide.

C.3 Makeup Removal Wipes for the Eyes

| | Formula | |
|---|---|---|
| A | Composition ($E_4$) | 3.00% |
| B | Sepicide ™ HB2 | 0.50% |
| C | Sepicalm ™ VG | 0.50% |
| | Fragrance/Scent | 0.05% |
| D | Water | Q.S. 100.00% |

Procedure:
The ingredients of phase B and also those of phase C are mixed in phase A until the solution is clear. Phase D is added.

C.4 Mild Foaming Gel

| | Formula | |
|---|---|---|
| A | Composition ($E_4$) | 8.50% |
| | Proteol ™ APL | 3.00% |
| | Euxyl ™ PE9010 | 1.00% |
| | Fragrance/scent | 0.10% |
| B | Water | Q.S. 100.00% |
| | Lactic acid | Q.S. pH = 6.0 |

Procedure:
Dissolve the fragrance and the Euxyl™ PE 9010 preservative in the mixture composed of the composition $E_4$ and of the Proteol™ APL (phase A). The water is added and the pH is adjusted to approximately 6.0 with lactic acid.

C.5 Frequent Use Shampoo

| | Formula | |
|---|---|---|
| A | Composition ($E_4$) | 12.80% |
| | Proteol ™ OAT | 5.00% |
| | Euxyl ™ PE 9010 | 1.00% |
| | Fragrance/Scent | 0.30% |
| | Water Q.S. | 100.00% |
| B | Montaline ™ C40 | 8.50% |
| | Lactic acid | Q.S. pH = 6.0 |

Procedure:
All the ingredients of phase A are mixed and, after homogenization, the Montaline™ C40 is added and the pH is adjusted to approximately 6.0 using lactic acid.

C.6 Ultra-Mild Baby Shampoo

| | Formula | |
|---|---|---|
| A | Composition ($E_4$) | 10.00% |
| | Amisoft ™ CS-11 | 4.00% |
| | Fragrance/Scent | 0.10% |
| | Sepicide ™ HB | 0.30% |
| | Sepicide ™ CI | 0.20% |
| | Water | Q.S. 100.00% |
| B | Water | 20.00% |
| | Capigel ™ 98 | 3.50% |
| | Tromethamine | Q.S. pH = 7.2. |

Procedure:
All the ingredients of phase A are mixed in the order indicated until a clear phase A is obtained. Separately, the Capigel™ 98 is added to the water, then this phase B thus prepared is added to phase A and the pH is adjusted to 7.2 using tromethamine

C.7 Cleansing Milk for Babies

| | Formula | |
|---|---|---|
| A | Simulsol ™ 165 | 2.00% |
| | Montanov ™ 202 | 1.00% |
| | Lanol ™ 99 | 3.00% |
| | Dimethicone | 1.00% |
| | Isohexadecane | 3.00% |
| B | Water | Q.S. 100.00% |
| C | Sepiplus ™ 400 | 0.30% |
| D | Composition ($E_4$) | 6.35% |
| E | Sepicide ™ HB | 0.30% |
| | DMDM hydantoin | 0.20% |
| | Fragrance/Scent | 0.10% |

Procedure:
Phases A and B, formed by mixing the various constituents, are heated separately. Phase C is added to the hot fatty phase and the emulsion is produced by running in the aqueous phase; the mixture is homogenized for a few minutes with vigorous stirring (by means of a rotor/stator turbine). Phase D is then added to the hot emulsion and the emulsion is cooled with moderate stirring until it has returned to ambient temperature. Phase E is added at 40° C.

C.8 Cleansing Powder Lotion for Sensitive Skin

| | Formula | | |
|---|---|---|---|
| A | Lipacide ™ C8G | 0.95% | |
| | Methyl paraben | 0.10% | |
| | Ethyl paraben | 0.024% | |
| | Propyl paraben | 0.0119% | |
| | Butyl paraben | 0.024% | |
| | Isobutyl paraben | 0.0119% | |
| | Water | 20.00% | |
| | Disodium EDTA | 0.10% | |
| | Triethanolamine | 1.38% | |
| B | Composition (E$_4$) | 1.80% | |
| | Fragrance/Scent | 0.10% | |
| C | Sepicalm ™ S | 0.28% | |
| | Water | Q.S. 100.00% | |
| | Lactic acid | Q.S. pH = 5.2 | |
| D | Micropearl ™ M310 | 5.00% | |

Procedure:

The ingredients of phase A are dissolved in the water at 80° C. The fragrance is dissolved separately in the composition (E$_4$) in order to prepare phase B. The cooled phase A is added to phase B, then the Sepicalm™ S is introduced along with the remainder to 100% made up of water. The final pH is verified and optionally adjusted to approximately 5.2. The Micropearl™ M310 is then added.

C.9 Shower Gel for Children

| | Formula | | |
|---|---|---|---|
| A | Water | 56.06% | |
| | Sepimax ™ Zen | 3.00% | |
| | Sepiplus ™ S | 0.80% | |
| B | Proteol ™ OAT | 20.80% | |
| | Oramix ™ NS 10 | 9.30% | |
| | Amonyl ™ 265 BA | 5.10% | |
| C | Composition (E$_4$) | 2.00% | |
| | Glyceryl glucoside | 1.00% | |
| | Phenoxyethanol & ethylhexylglycerin | 1.00% | |
| | Fragrance/Scent | 0.90% | |
| | Dye | 0.04% | |

Procedure:

The Sepimax™ ZEN is dispersed in the water and the mixture is stirred using a mechanical stirrer equipped with a deflocculator, a counter propeller and a paddle of anchor type, until a perfectly smooth gel is obtained. The Sepi-plus™ S is added and then stirring is carried out until the mixture is homogeneous. The ingredients of phase B are then added, the mixture is homogenized and the additives of phase C are added individually. The pH is adjusted to 6.0-6.5.

C.10 BB Cream

| | Formula | | |
|---|---|---|---|
| A | Easynov ™ | 2.30% | |
| | Lanol ™ 99 | 1.00% | |
| | Sepimat ™ H10W | 1.00% | |
| | Ethylhexyl methoxycinnamate | 5.00% | |
| B | Cyclomethicone | 6.00% | |
| | Triethoxycaprylsilane & Alumina-silane & Titanium Oxide | 8.00% | |
| | Iron Oxide red & Triethoxycaprylsilane | 0.24% | |
| | Iron Oxide yellow & Triethoxycaprylsilane | 0.66% | |
| | Iron Oxide black & Triethoxycaprylsilane | 0.09% | |
| | Fragrance/Scent | 0.10% | |
| C | Water | qs 100% | |
| | Sepinov ™ EMT10 | 1.20% | |
| D | Composition (E$_4$) | 2.00% | |
| | Sepitonic ™ M3 | 1.00% | |
| | Phenoxyethanol & Ethylhexylglycerin | 1.00% | |

Procedure:

Phase B is prepared by mixing the various ingredients and homogenizing using a mixer equipped with a rotor-stator system at a rotational speed of 4500 revolutions per minute, for a period of 6 minutes. Phase C is prepared by adding the Sepinov™ EMT10 to the mixture of water and glycerol and homogenizing using a mixer equipped with a rotor-stator system at a rotational speed of 4000 revolutions per minute for 4 minutes. Phases A and B are added to phase C, and the resulting mixture is stirred using a mechanical stirrer equipped with a paddle of anchor type, at a speed of 30 revolutions per minute for 2 minutes, then at a speed of 50 revolutions per minute for 20 minutes. The components of phase D are added one by one and the mixture is stirred at a speed of 50 revolutions per minute for 25 minutes.

C.11 High-Protection Sun Spray, SPH Greater than 30

| | Formula | | |
|---|---|---|---|
| A | Montanov ™ L | 1.00% | |
| | Montanov ™ 82 | 1.00% | |
| | C12-15 alkyl benzoate | 17.00% | |
| | Dimethicone | 3.00% | |
| | Octocrylene | 6.00% | |
| | Ethylhexyl methoxycinnamate | 6.00% | |
| | Bis-ethylhexyloxyphenol Methoxyphenyl Triazine | 3.00% | |
| | Tocopherol | 0.05% | |
| B | Water | qs 100% | |
| C | Simulgel ™ INS 100 | 0.50% | |
| | Cyclodimethicone | 5.00% | |
| D | Composition (E$_4$) | 3.00% | |
| | Phenoxyethanol & Ethylhexylglycerin | 1.00% | |
| | Fragrance/Scent | 0.20% | |
| E | Methylene bis-benzotriazolyl Tetramethylbutylphenol | 10.00% | |
| | 25% citric acid | qs pH = 5 | |

Sepicalm™ S: mixture of N-cocoylamino acids, of sarcosine, of potassium aspartate and of magnesium aspartate as described in WO 98/09611.

Proteol™ APL: mixture of sodium salts of N-cocoylamino acids, obtained by acylation of the characteristic amino acids of apple juice;

Sepicide™ HB: mixture of phenoxyethanol, of methyl paraben, of ethyl paraben, of propyl paraben and of butyl paraben, is a preservative;

Capigel™ 98: acrylate copolymer;

Sepicide™ CI: imidazoline urea, is a preservative;

Sepicide™ HB: mixture of phenoxyethanol, of methyl paraben, of ethyl paraben, of propyl paraben, of butyl paraben and of isobutyl paraben, is a preservative;

Sepicalm™ VG: mixture of N-palmitoylproline in sodium salt form and of extract of flowers of Nymphea alba;

Euxyl™ PE9010: mixture of phenoxyethanol and of ethylhexylglycerin;

Proteol™ OAT: mixture of N-laurylamino acids obtained by total hydrolysis of oat protein, as described in WO 94/26694;

Montaline™ C40: monoethanolamine cocamidopropyl betainamide chloride salt;

Amisoft™ CS-11: sodium salt of N-cocoylglutamate;

Simulsol™ 165: mixture of PEG-100 stearate and of glyceryl stearate;

Montanov™ 202 (arachidyl alcohol, behenyl alcohol and arachidyl glucoside), is a self-emulsifiable composition such as those described in EP 0 977 626;

Lanol™ 99: isononyl isononanoate;

Sepiplus™ 400: self-invertible inverse latex of polyacrylates in polyisobutylene which comprises polysorbate 20, as described in WO 2005/040230;

Lipacide™ C8G: capryloyl glycine sold by the company Seppic;

Micropearl™ M310: crosslinked polymethyl methacrylate polymer which is provided in powder form and is used as a texture modifier;

Sepimax™ Zen (INCI name: Polyacrylate Crosspolymer-6): thickening polymer which is provided in the form of a powder;

Sepiplus™ S (INCI name: Hydroxyethyl Acrylate/Sodium Acryloyldimethyl Taurate Copolymer & Polyisobutene & PEG-7 Trimethylolpropane Coconut Ether): self-invertible inverse latex;

Amonyl™ 265 BA (INCI name: Cocobetaine): foaming amphoteric surfactant;

Sepinov™ EMT10 (INCI name: Hydroxyethyl Acrylate/Sodium Acryloyldimethyl Taurate Copolymer): thickening copolymer which is provided in the form of a powder;

Easynov™ (INCI name: Octyldodecanol and Octyldodecyl Xyloside and PEG-30 Dipolyhydroxystearate): emulsifying agent having a lipophilic tendency;

Sepimat™ H10 FW (INCI name: Methyl Methacrylate Crosspolymer and Squalane): polymer used as a texturing agent;

Sepitonic™ M3 (INCI name: Magnesium Aspartate and Zinc Gluconate and Copper Gluconate): mixture used as a free-radical scavenger and an energizing agent for cells;

Montanov™ L (INCI name: C14-22 Alcohols and C12-20 Alkylglucoside): emulsifying agent;

Montanov™ 82 (INCI name: Cetearyl Alcohol and Cocoglucoside): emulsifying agent;

Simulgel™ INS100 (INCI name: Hydroxyethyl Acrylate/Sodium Acryloyldimethyl Taurate Copolymer and isohexadecane and Polysorbate 60): polymeric thickener.

The invention claimed is:

1. A process for short-term improvement of the moisturization state of the stratum corneum of human skin epidermis, the process comprising:
  applying, to the surface of the skin to be treated, an effective amount of a composition for topical application (C) comprising:
    at least one cosmetically acceptable excipient (E), and
    a composition ($C_1$) consisting of, for 100% of the weight thereof:
  (a)—from 20% by weight to 50% by weight of at least one composition ($C_2$), said composition ($C_2$) consisting of, for 100% of the weight thereof:
    (1)—from 3% to 25% by weight of a polyol of formula (I):

HO—CH$_2$—(CHOH)$_m$—CH$_2$—OH  (I);

in which formula (I) m represents an integer equal to 2, 3 or 4;
    (2)—from 25% to 45% by weight of one or more anhydrides of said polyol of formula (I);
    (3)—from 30% to 72% by weight of a composition ($C_A$) represented by formula (II):

HO—CH$_2$—(CHOH)$_m$—CH$_2$—O-(G)$_x$-H  (II), in which formula (II) G represents the residue of a reducing sugar, m is as previously defined in formula (I) and x, which indicates the average degree of polymerization of said residue G, represents a decimal number greater than 1 and less than or equal to 5, and
    (4)—the remainder to 100% by weight being made up of water; and
  (b)—from 50% by weight to 80% by weight of at least one compound of formula (III):

HO—[CH$_2$—CH(OH)—CH$_2$—O]$_p$—H  (III), in which formula (III) p represents an integer greater than or equal to 1 and less than or equal to 6,
  it being understood that, in said composition ($C_1$), the composition ($C_A$)/compound of formula (III) weight ratio is greater than or equal to 1/10 and less than or equal to 1/2.

2. The process as defined in claim 1, wherein, in formula (II), said residue G of a reducing sugar is selected from the residues of glucose, of xylose and of arabinose.

3. The process as defined in claim 1, wherein, in formula (II), x represents a decimal number greater than or equal to 1.05 and less than or equal to 3.0.

4. The process as defined in claim 1, wherein, in formulae (I) and (II), n is equal to 3.

5. The process as defined in claim 1, wherein, in formula (III), p represents an integer equal to 1.

6. The process as defined in claim 2, wherein, in formula (II), x represents a decimal number greater than or equal to 1.05 and less than or equal to 3.0.

7. The process as defined in claim 2, wherein, in formulae (I) and (II), n is equal to 3.

8. The process as defined in claim 3, wherein, in formulae (I) and (II), n is equal to 3.

9. The process as defined in claim 2, wherein, in formula (III), p represents an integer equal to 1.

10. The process as defined in claim 3, wherein, in formula (III), p represents an integer equal to 1.

11. The process as defined in claim 4, wherein, in formula (III), p represents an integer equal to 1.

12. A composition ($C_1$) consisting of, for 100% of the weight thereof:
  (a)—from 20% by weight to 50% by weight of at least one composition ($C_2$), said composition ($C_2$) consisting of, for 100% of the weight thereof:
    (1)—from 3% to 25% by weight of a polyol of formula (I):

HO—CH$_2$—(CHOH)$_m$—CH$_2$—OH  (I);

in which formula (I) m represents an integer equal to 2, 3 or 4;
    (2)—from 25% to 45% by weight of one or more anhydrides of said polyol of formula (I);
    (3)—from 30% to 72% by weight of a composition ($C_A$) represented by formula (II):

HO—CH$_2$—(CHOH)$_m$—CH$_2$—O-(G)$_x$-H  (II), in which formula (II) G represents the residue of a reducing sugar, m is as previously defined in formula (I) and x, which indicates the average degree of polymerization of said residue G, represents a decimal number greater than 1 and less than or equal to 5, and (4)—the remainder to 100% by weight being made up of water; and (b)—from 50% by weight to 80% by weight of at least one compound of formula (III):

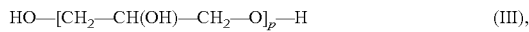

HO—[CH$_2$—CH(OH)—CH$_2$—O]$_p$—H　　(III), in which formula (III) p represents an integer greater than or equal to 1 and less than or equal to 6, it being understood that, in said composition (C$_1$), the composition (C$_A$)/compound of formula (III) weight ratio is greater than or equal to 1/10 and less than or equal to 1/2.

13. The composition (C$_1$) as defined in claim 12, wherein, in formula (II), said residue G of a reducing sugar is selected from the residues of glucose, xylose and arabinose, and x represents a decimal number greater than or equal to 1.05 and less than or equal to 3.0.

14. The composition (C$_1$) as defined in claim 12, wherein, in formulae (I) and (II), m is equal to 2, in formula (II) said residue G represents the residue of glucose, and x represents a decimal number between 1.05 and 2.5, and, in formula (III), p is equal to 1 or equal to 2.

15. The composition (C$_1$) as defined in claim 12, wherein, in formulae (I) and (II), m is equal to 3, in formula (II), said residue G represents the residue of glucose, and x represents a decimal number between 1.05 and 2.5, and, in formula (III), p is equal to 1 or equal to 2.

16. The composition (C$_1$) as defined in claim 12, wherein, in formulae (I) and (II), m is equal to 4, in formula (II), said residue G represents the residue of glucose, and x represents a decimal number between 1.05 and 2.5, and, in formula (III), p is equal to 1 or equal to 2.

17. The composition (C$_1$) as defined in claim 13, wherein, in formulae (I) and (II), m is equal to 2, in formula (II) said residue G represents the residue of glucose, and x represents a decimal number between 1.05 and 2.5, and, in formula (III), p is equal to 1 or equal to 2.

18. The composition (C$_1$) as defined in claim 13, wherein, in formulae (I) and (II), m is equal to 3, in formula (II), said residue G represents the residue of glucose, and x represents a decimal number between 1.05 and 2.5, and, in formula (III), p is equal to 1 or equal to 2.

19. The composition (C$_1$) as defined in claim 13, wherein, in formulae (I) and (II), m is equal to 4, in formula (II), said residue G represents the residue of glucose, and x represents a decimal number between 1.05 and 2.5, and, in formula (III), p is equal to 1 or equal to 2.

* * * * *